(12) United States Patent
Guo et al.

(10) Patent No.: US 11,198,121 B1
(45) Date of Patent: Dec. 14, 2021

(54) FLOW CELL SYSTEMS AND DEVICES

(71) Applicant: Element Biosciences, Inc., San Diego, CA (US)

(72) Inventors: Minghao Guo, San Diego, CA (US); Leon Zilun Zhang, San Diego, CA (US); Chunhong Zhou, San Diego, CA (US); Matthew Kellinger, San Diego, CA (US); Michael Previte, San Diego, CA (US); Sinan Arslan, San Diego, CA (US); Molly He, San Diego, CA (US); Hui Zhen Mah, San Diego, CA (US); Lei Sun, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 17/218,027

(22) Filed: Mar. 30, 2021

Related U.S. Application Data

(60) Provisional application No. 63/037,558, filed on Jun. 10, 2020.

(51) Int. Cl.
| | | |
|---|---|---|
| *G01N 21/64* | (2006.01) | |
| *B01L 3/00* | (2006.01) | |
| *C12Q 1/6874* | (2018.01) | |
| *C12N 15/10* | (2006.01) | |
| *C12Q 1/6806* | (2018.01) | |

(52) U.S. Cl.
CPC ... *B01L 3/502715* (2013.01); *B01L 3/502738* (2013.01); *C12N 15/1003* (2013.01); *C12Q 1/6806* (2013.01); *C12Q 1/6874* (2013.01); *G01N 21/6428* (2013.01); *B01L 2300/0816* (2013.01); *B01L 2400/0478* (2013.01); *B01L 2400/0644* (2013.01); *G01N 2021/6439* (2013.01)

(58) Field of Classification Search
CPC ........... G01N 21/6428; G01N 21/6486; G01N 21/64; G01N 21/63; G01N 21/62; G01N 2021/6439
USPC .......................................... 422/503; 436/180
See application file for complete search history.

(56) References Cited

U.S. PATENT DOCUMENTS

| | | | |
|---|---|---|---|
| 5,512,131 A | 4/1996 | Kumar et al. | |
| 5,547,839 A | 8/1996 | Dower et al. | |
| 5,622,872 A | 4/1997 | Ribi | |
| 6,720,143 B2 | 4/2004 | Juncosa et al. | |
| 8,143,599 B2 | 3/2012 | Feng et al. | |
| 8,242,463 B2 | 8/2012 | Feng et al. | |
| 8,341,097 B2 | 12/2012 | Meng et al. | |
| 8,399,196 B2 * | 3/2013 | Hoser | C07H 19/00 435/6.12 |
| 8,637,650 B2 | 1/2014 | Cherkasov et al. | |
| 9,014,989 B2 | 4/2015 | McMillen et al. | |
| 9,068,220 B2 | 6/2015 | Feng et al. | |
| 9,365,898 B2 | 6/2016 | Feng et al. | |
| 9,552,458 B2 | 1/2017 | White et al. | |
| 9,600,625 B2 | 3/2017 | Asadi et al. | |
| 9,940,266 B2 | 4/2018 | Van Rooyen et al. | |
| 10,049,179 B2 | 8/2018 | Van Rooyen et al. | |
| 10,068,054 B2 | 9/2018 | Van Rooyen et al. | |
| 10,068,183 B1 | 9/2018 | Van Rooyen | |
| 10,509,795 B2 | 12/2019 | Farh et al. | |
| 10,607,156 B2 | 3/2020 | Farh et al. | |
| 10,691,775 B2 | 6/2020 | Van Rooyen et al. | |
| 10,704,094 B1 | 7/2020 | Arslan et al. | |
| 10,768,173 B1 | 9/2020 | Arslan et al. | |
| 10,787,573 B2 | 9/2020 | Zheng et al. | |
| 10,876,148 B2 | 12/2020 | Zhou et al. | |
| 10,919,033 B2 | 2/2021 | Ren et al. | |
| 10,982,280 B2 | 4/2021 | Arslan et al. | |
| 11,053,540 B1 | 7/2021 | Chen et al. | |
| 11,060,138 B1 | 7/2021 | Chen et al. | |
| 2004/0248287 A1 | 12/2004 | Hu et al. | |
| 2009/0186775 A1 | 7/2009 | Nowak et al. | |
| 2010/0298171 A1 | 11/2010 | Shirazi et al. | |
| 2011/0111975 A1 | 5/2011 | Schneider et al. | |
| 2018/0121601 A1 | 5/2018 | Hahm et al. | |
| 2018/0178215 A1 | 6/2018 | Fisher et al. | |
| 2019/0348149 A1 | 11/2019 | Chen et al. | |
| 2019/0371430 A1 | 12/2019 | Ng et al. | |
| 2020/0149095 A1 | 5/2020 | Arslan et al. | |
| 2020/0370113 A1 | 11/2020 | Kellinger et al. | |
| 2021/0040534 A1 | 2/2021 | Zhou et al. | |
| 2021/0072234 A1 | 3/2021 | Arslan et al. | |
| 2021/0121882 A1 | 4/2021 | Guo et al. | |
| 2021/0123098 A1 | 4/2021 | Previte et al. | |
| 2021/0123911 A1 | 4/2021 | Arslan et al. | |
| 2021/0139884 A1 | 5/2021 | Kellinger et al. | |
| 2021/0139981 A1 | 5/2021 | Arslan et al. | |

FOREIGN PATENT DOCUMENTS

| | | |
|---|---|---|
| DE | 10014204 A1 | 10/2001 |
| WO | WO-2017123664 A1 | 7/2017 |

(Continued)

OTHER PUBLICATIONS

Wong, Development of a quantitative assay for SARS coronavirus and correlation of GAPDH mRNA with SARS coronavirus in clinical specimens, J Clin Pathol, Feb. 25, 2005, pp. 276-280. (Year: 2005).*
Berki et al., Advanced Fluorescent Polymer Probes for the Site-Specific Labeling of Proteins in Live Cells Using the HaloTag Technology. ACS Omega 4: 12841-12847 (2019).
Dubber et al., Solid Phase Synthesis and Multivalent Glycoconjugates on a DNA Synthesizer. Bioconjugate Chem 14: 239-246 (2003).

(Continued)

*Primary Examiner* — Christine T Mui
(74) *Attorney, Agent, or Firm* — Wilson Sonsini Goodrich & Rosati

(57) ABSTRACT

Flow cell devices, cartridges, and systems are described that provide reduced manufacturing complexity, lowered consumable costs, and flexible system throughput for nucleic acid sequencing and other chemical or biological analysis applications. The flow cell device can include a capillary flow cell device or a microfluidic flow cell device.

20 Claims, 12 Drawing Sheets

(56) References Cited

FOREIGN PATENT DOCUMENTS

| WO | WO-2018006022 A1 | 1/2018 |
| WO | WO-2019241305 A1 | 12/2019 |
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |

OTHER PUBLICATIONS

Duret et al., Labeling of native proteins with fluorescent RAFT polymer probes: Application to the detection of a cell surface protein using flow cytometry. Polym. Chem. 9: 1857-1868 (2018).

Enhanced sequencing capabilities with the NovaSeq 6000 v1.5 Reagent Kit. Illumina (2020). 2 pages.

Favier et al., Synthesis on N-acryloxysuccinimide copolymers by RAFT polymerization, as reactive building blocks with full control of composition and molecular weights. Polymer 45: 7821-7830 (2004).

Huntsman Cancer Institute High-Throughput Genomics and Bioinformatic Analysis Shared Resource. NovaSeq 6000. University of Utah Huntsman Cancer Institute. (2021). 6 pages.

Illumina COVIDSeq Test. Key Features and Benefits. (2021). 5 pages.

Illumina DRAGEN Bio-IT. Frequently Asked Questions. (2021).

Introducing the NovaSeq 6000 v1.5 reagents. Illumina (2020). 3 pages.

MiSeq System. Speed and simplicity for targeted resequencing and small-genome sequencing (2021). 5 pages.

NovaSeq 6000 Sequencing System. Illumina (2020). 4 pages.

\* cited by examiner

1 Piece

- 1 Layer
- 12 Slide's per 8 Inch (210mm) Wafer

2 Piece

- 2 Layer's
- 12 Slide's per 8 Inch (210mm) Wafer

3 Piece

- 3 Layer's
- 12 Slide's per 8 Inch (210mm) Wafer

FLOW CELL SYSTEMS AND DEVICES

CROSS-REFERENCE

This application claims the benefit of U.S. Provisional Application No. 63/037,558, filed Jun. 10, 2020, which is incorporated herein by reference in its entirety.

BACKGROUND

Flow-cell devices are widely used in chemistry and biotechnology applications. Particularly in next-generation sequencing (NGS) systems, such devices are used to immobilize template nucleic acid molecules derived from biological samples and then introduce a repetitive flow of sequencing-by-synthesis reagents to attach labeled nucleotides to specific positions in the template sequences. A series of label signals are detected and decoded to reveal the nucleotide sequences of the template molecules, e.g., immobilized and/or amplified nucleic acid template molecules attached to an internal surface of the flow cell.

Typical NGS flow cells are multi-layer structures fabricated from planar surface substrates and other flow cell components (see, for example, U.S. Patent Application Publication No. 2018/0178215 A1), which are then bonded through mechanical, chemical, or laser bonding techniques to form fluid flow channels. Such flow cells typically require costly multi-step, precision fabrication techniques to achieve the required design specifications. On the other hand, inexpensive and off-the-shelf, single lumen (flow channel) capillaries are available in a variety of sizes and shapes but are generally not suited for ease of handling and compatibility with the repetitive switching between reagents that are required for application such as NGS.

SUMMARY

Described herein are novel flow cell devices and systems for sequencing nucleic acids. The devices and systems described herein can achieve a more efficient use of the reagents help reduce the cost and time of the DNA sequencing process. The devices and systems can utilize a commercially-available, off-the-shelf capillaries or a micro or nano scale fluidic chip with a selected pattern of channels. The flow cell devices and systems described herein are suitable for rapid DNA sequencing and can help achieve more efficient use of expensive reagents and reduce the amount of time required for sample pre-treatment and replication compared to other DNA sequencing techniques. The result is a much faster and cost-effective sequencing method.

Some embodiments related to methods of processing a sample of a subject having or suspected of having Coronavirus Disease 2019 (COVID-19) caused by a severe respiratory syndrome 2 (SARS-CoV-2) virus, said method comprising: (a) providing a nucleic acid sequencing flow cell comprising two or more microfluidic channels, wherein at least one of said two or more microfluidic channels comprises a surface comprising a nucleic acid sequence immobilized thereto, wherein said nucleic acid sequence is derived from said sample of said subject having or suspected of having said COVID-19; (b) contacting said nucleic acid sequence with a primer having complementarity with said nucleic acid sequence, to yield a primed nucleic acid sequence; (c) using at least (i) a polymerizing enzyme and (ii) plurality of nucleobases having a plurality of detectable labels to subject said primed nucleic acid sequence to a primer extension reaction; (d) while performing said primer extension reaction, using a detector to detect a plurality of signals from at least a subset of said plurality of detectable labels; and (e) using said plurality of signals detected in (d) to generate sequencing data; (f) processing said sequencing data using parallel processing using one or more logic circuits to identify said nucleic acid sequence; (g) using said nucleic acid sequence identified in (f) to determine that said sample contains a messenger ribonucleic acid (mRNA) molecule encoding said SARS-CoV-2. In some embodiments, said plurality of detectable labels comprises a plurality of fluorophores. In some embodiments, said using said plurality of signals detected in (d) to identify said nucleic acid sequence comprises imaging a first surface and an axially-displaced second surface of said two or more microfluidic channels using a fluorescent imaging system. In some embodiments, methods further comprising, before (a): (h) introducing a fluid composition comprising said nucleic acid sequence at a concentration of between about 0.5 nanomolar (nM) and 900 nm to said nucleic acid sequencing flow cell. In some embodiments, methods further comprise, before (a): (i) hybridizing at least a portion of said nucleic acid sequence to at least a portion of oligonucleotides grafted to said surface. In some embodiments, said nucleic acid sequencing flow cell is loaded with said fluid composition prior to (c). In some embodiments, said nucleic acid sequences are present at said surface at a surface density comprising at least 4,000 molecules per square micrometer ($\mu^2$). In some embodiments, said surface is salinized and said capture oligonucleotides are covalently grafted to said surface. In some embodiments, said at least one of said two or more microfluidic channels is configured to hold a fluid volume between about 10 to about 300 microliters. In some embodiments, a fluorescent image of said surface exhibits a contrast-to-noise ratio of at least or equal to about 5 when said fluorescent image of said surface is obtained with an inverted fluorescence microscope and a camera under non-signal saturating conditions while said surface is immersed in a buffer, and said plurality of detectable labels comprise Cyanine dye-3. In some embodiments, said nucleic acid sequence has a length comprising more than or equal to about 100 base pairs. In some embodiments, said nucleic acid sequencing flow cell comprises a flow cell cartridge that mates with said microfluidic chip. In some embodiments, methods further comprise, before (a): (j) extracting said mRNA from said sample; and (k) converting said mRNA to complementary DNA comprising said nucleic acid sequence. In some embodiments, said sample comprises epithelial cells. In some embodiments, said one or more logic circuits comprises a field programmable gate array (FPGA). In some embodiments, said sequencing data is further analyzed using a central processing unit (CPU). In some embodiments, said parallel processing is performed is Cloud-based computing. In some embodiments, said two or more microfluidic channels comprises four microfluidic channels. In some embodiments, methods further comprise amplifying said nucleic acid sequence prior to (a) or (b) using polymerase chain reaction (PCR). In some embodiments, said performing said primer extension reaction comprises performing a sequencing-by-synthesis reaction.

Some embodiments relate to a flow cell device, comprising: a first reservoir housing a first solution and having an inlet end and an outlet end, wherein the first agent flows from the inlet end to the outlet end in the first reservoir; a second reservoir housing a second solution and having an inlet end and an outlet end, wherein the second agent flows from the inlet end to the outlet end in the second reservoir; a central region having an inlet end fluidically coupled to the outlet end of the first reservoir and the outlet end of the second reservoir through at least one valve; wherein the volume of the first solution flowing from the outlet of the first reservoir to the inlet of the central region is less than the volume of the second solution flowing from the outlet of the second reservoir to the inlet of the central region.

Some embodiments relate to a flow cell device comprising: a framework; a plurality of reservoirs harboring reagents common to a plurality of reactions compatible with the flow cell; a single reservoir harboring a reaction-specific reagent; a removable capillary having 1) a first diaphragm valve gating intake of a plurality of nonspecific reagents from the plurality of reservoirs, and 2) a second diaphragm valve gating intake of a single reagent from a source reservoir in close proximity to the second diaphragm valve.

Some embodiments relate to a flow cell device comprising: a flame work; a plurality of reservoirs harboring reagents common to a plurality of reactions compatible with the flow cell; a single reservoir harboring a reaction-specific reagent; a removable or non-removable capillary having 1) a first diaphragm valve gating intake of a plurality of nonspecific reagents from the plurality of reservoirs, and 2) a second diaphragm valve gating intake of a single reagent from a source reservoir in close proximity to the second diaphragm valve. 3) optionally, a mounting embodiment whereby capillaries are affixed/mounted to glass substrate via an index mounting media.

Some embodiments relate to a flow cell device comprising: a) one or more capillaries, wherein the one or more capillaries are replaceable; b) two or more fluidic adaptors attached to the one or more capillaries and configured to mate with tubing that provides fluid communication between each of the one or more capillaries and a fluid control system that is external to the flow cell device; and c) optionally, a cartridge configured to mate with the one or more capillaries such that the one or more capillaries are held in a fixed orientation relative to the cartridge, and wherein the two or more fluidic adaptors are integrated with the cartridge, optionally, a mounting embodiment whereby capillaries are affixed/mounted to glass substrate via an index mounting media.

Some embodiments relate to a method of sequencing a nucleic acid sample and a second nucleic acid sample, comprising: delivering a plurality of oligonucleotides to an interior surface of an at least partially transparent chamber; delivering a first nucleic acid sample to the interior surface; delivering a plurality of nonspecific reagents through a first channel to the interior surface; delivering a specific reagent through a second channel to the interior surface, wherein the second channel has a lower volume than the first channel; visualizing a sequencing reaction on the interior surface of the at least partially transparent chamber; and replacing the at least partially transparent chamber prior to a second sequencing reaction.

Some embodiments relate to a method of reducing a reagent used in a sequencing reaction, comprising: providing a first reagent in a first reservoir; providing a second reagent in a first second reservoir, wherein each of the first reservoir and the second reservoir are fluidically coupled to a central region, and wherein the central region comprises a surface for the sequencing reaction; and sequentially introducing the first reagent and the second reagent into a central region of the flow cell device, wherein the volume of the first reagent flowing from the first reservoir to the inlet of the central region is less than the volume of the second reagent flowing from the second reservoir to the central region.

Some embodiments relate to a method of increasing the efficient use of a regent in a sequencing reaction, comprising: providing a first reagent in a first reservoir; providing a second reagent in a first second reservoir, wherein each of the first reservoir and the second reservoir are fluidically coupled to a central region, and wherein the central region comprises a surface for the sequencing reaction; and maintaining the volume of the first reagent flowing from the first reservoir to the inlet of the central region to be less than the volume of the second reagent flowing from the second reservoir to the central region.

Some embodiments relate to a method wherein the first reagent is more expensive than the second agent. Other embodiments relate to a method wherein the first reagent is selected from the group consisting of a polymerase, a nucleotide, and a nucleotide analog.

Certain circumstances relate to a method of detecting a pathogen, comprising contacting a sample with a one or more binding moieties wherein said binding moieties are immobilized on one or more surfaces of a flow cell, said surfaces comprising one or more layers of a hydrophilic coating, thereby immobilizing one or more nucleic acid components of said sample for analysis. Other circumstances relate to a method wherein one or more nucleic acid components comprise a viral nucleic acid.

Some embodiments relate to a method of detecting a pathogen, comprising contacting a sample with a one or more oligonucleotides tethered to the interior surface of a flow cell comprising one or more layers of a hydrophilic coating, and wherein the one or more oligonucleotides exhibit a segment that specifically hybridizes to a viral nucleic acid segment. Further, some embodiments, relate to a method comprising one or more nucleic acid sequencing steps, wherein said sequencing step comprises a sequencing by binding step or wherein said sequencing step comprises a sequencing by synthesis step.

Certain instances relate to a method comprising a nucleic acid amplification step, wherein said amplification step is carried out on the surface of one or more flow cells.

Some embodiments relate to a method comprising hybridizing a tethered oligonucleotide to a viral nucleic acid, the method further comprising a detection step, wherein the detection step is a fluorescence detection step.

Certain circumstances comprise contacting a nucleic acid with a fluorescent label.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

Some novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9A shows the preparation of one-piece glass flow cell; FIG. 9B shows the preparation of two-piece glass flow cell; and FIG. 9C shows the preparation of three-piece glass flow cell.

FIG. 10A shows an one-piece glass flow cell design; FIG. 10B shows a two-piece glass flow cell design; and FIG. 10C shows a three-piece glass flow cell design.

DETAILED DESCRIPTION

Figure 1:
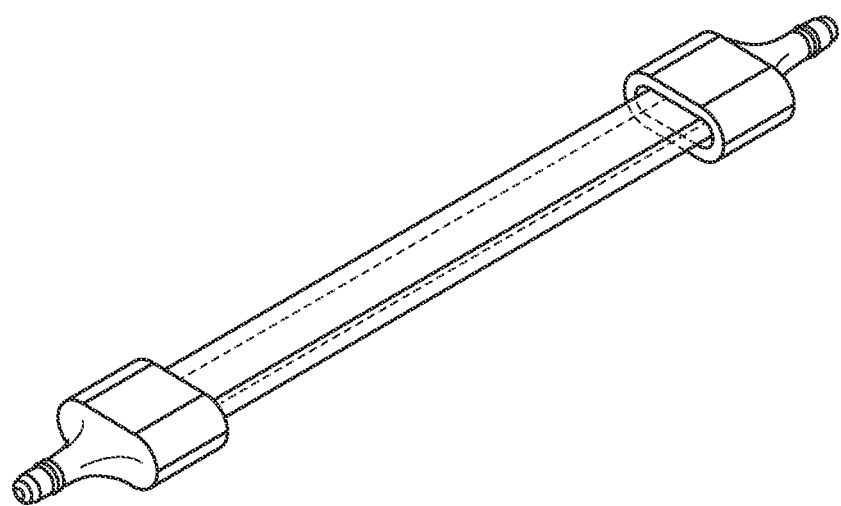
FIG. 1 illustrates one embodiment of a single capillary flow cell having 2 fluidic adaptors.

Described herein are systems and devices to analyze a large number of different nucleic acid sequences from e.g., amplified nucleic acid arrays in flow cells or from an array of immobilized nucleic acids. The systems and devices described herein can also be useful in, e.g., sequencing for comparative genomics, tracking gene expression, micro RNA sequence analysis, epigenomics, and aptamer and phage display library characterization, and other sequencing applications. The systems and devices herein comprise various combinations of optical, mechanical, fluidic, thermal, electrical, and computing devices/aspects. The advantages conferred by the disclosed flow cell devices, cartridges, and systems include, but are not limited to: (i) reduced device and system manufacturing complexity and cost, (ii) significantly lower consumable costs (e.g., as compared to those for currently available nucleic acid sequencing systems), (iii) compatibility with typical flow cell surface functionalization methods, (iv) flexible flow control when combined with microfluidic components, e.g., syringe pumps and diaphragm valves, etc., and (v) flexible system throughput.

Described herein are capillary flow-cell devices and capillary flow cell cartridges that are constructed from off-the-shelf, disposable, single lumen (e.g., single fluid flow channel) capillaries that may also comprise fluidic adaptors, cartridge chassis, one or more integrated fluid flow control components, or any combination thereof. Also disclosed herein are capillary flow cell-based systems that may comprise one or more capillary flow cell devices, one or more capillary flow cell cartridges, fluid flow controller modules, temperature control modules, imaging modules, or any combination thereof.

The design features of some disclosed capillary flow cell devices, cartridges, and systems include, but are not limited to, (i) unitary flow channel construction, (ii) sealed, reliable, and repetitive switching between reagent flows that can be implemented with a simple load/unload mechanism such that fluidic interfaces between the system and capillaries are reliably sealed, facilitating capillary replacement and system reuse, and enabling precise control of reaction conditions such as temperature and pH, (iii) replaceable single fluid flow channel devices or capillary flow cell cartridges comprising multiple flow channels that can be used interchangeably to provide flexible system throughput, and (iv) compatibility with a wide variety of detection methods such as fluorescence imaging.

Although the disclosed single flow cell devices and systems, capillary flow cell cartridges, capillary flow cell-based systems, microfluidic chip flow cell device, and microfluidic chip flow cell systems, are described primarily in the context of their use for nucleic acid sequencing applications, various aspects of the disclosed devices and systems may be applied not only to nucleic acid sequencing but also to any other type of chemical analysis, biochemical analysis, nucleic acid analysis, cell analysis, or tissue analysis application. It shall be understood that different aspects of the disclosed devices and systems can be appreciated individually, collectively, or in combination with each other.

Definitions: Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated.

As used herein, the term 'about' a number refers to that number plus or minus 10% of that number. The term 'about' when used in the context of a range refers to that range minus 10% of its lowest value and plus 10% of its greatest value.

As used herein, the phrase 'at least one of' in the context of a series encompasses lists including a single member of the series, two members of the series, up to and including all members of the series, alone or in some cases in combination with unlisted components.

As used herein, fluorescence is 'specific' if it arises from fluorophores that are annealed or otherwise tethered to the surface, such as through a nucleic acid having a region of reverse complementarity to a corresponding segment of an oligo on the surface and annealed to said corresponding segment. This fluorescence is contrasted with fluorescence arising from fluorophores not tethered to the surface through such an annealing process, or in some cases to background florescence of the surface.

Nucleic acids: As used herein, a "nucleic acid" (also referred to as a "polynucleotide", "oligonucleotide", ribonucleic acid (RNA), or deoxyribonucleic acid (DNA)) is a linear polymer of two or more nucleotides joined by covalent internucleosidic linkages, or variants or functional fragments thereof. In naturally occurring examples of nucleic acids, the internucleoside linkage is typically a phosphodiester bond. However, other examples optionally comprise other internucleoside linkages, such as phosphorothiolate linkages and may or may not comprise a phosphate group.

Nucleic acids include double- and single-stranded DNA, as well as double- and single-stranded RNA, DNA/RNA hybrids, peptide-nucleic acids (PNAs), hybrids between PNAs and DNA or RNA, and may also include other types of nucleic acid modifications. Also, as used herein, nucleic acids may comprise nucleic acid portions of human, animal, or plant pathogens, such as fungi, bacteria, archaea, eukaryotic parasites, protozoa, or viruses, including but not limited to, filoviruses, coronaviruses, adenoviruses, retroviruses, and the like. Exemplary viruses having nucleic acid components contemplated in this disclosure include but are not limited to ebola virus, Marburg virus other filoviruses, alpha coronaviruses (such as 229E and NL63), beta coronaviruses (such as OC43 and HKU1), other coronaviruses, such as MERS-CoV, SARS-COV, 2019-nCoV and SARS-CoV-2), retroviruses (such as the Human Immunodeficiency Virus and Feline Immunodeficiency Virus), Adenoviruses, Influenza Viruses (including H1N1 and H5N1 subtypes, but contemplating all subtypes and combinations of influenza viruses), poxviruses, herpesviruses, and the like. Additional viral nucleic acids contemplated herein include but are not limited to nucleic acid components of vegetable mosaic viruses (tomato mosaic virus, tobacco mosaic virus, cucumber mosaic virus), and viruses related to common animal diseases, including rabies virus. Similarly contemplated as nucleic acids within the current disclosure are viroids and subviral pathogens such as hepatitis delta RNA, Citrus exocortis viroid, Columnea latent viroid, Pepper chat fruit viroid, Potato spindle tuber viroid, Tomato chlorotic dwarf viroid, coconut cadang-cadang viroid, and Tomato apical stunt viroid, and the like.

As used herein, a "nucleotide" refers to a nucleotide, nucleoside, or analog thereof. In some cases, the nucleotide is an N- or C-glycoside of a purine or pyrimidine base (e.g., a deoxyribonucleoside containing 2-deoxy-D-ribose or ribonucleoside containing D-ribose). Examples of other nucleotide analogs include, but are not limited to, phosphorothioates, phosphoramidates, methyl phosphonates, chiral-methyl phosphonates, 2-O-methyl ribonucleotides, and the like.

Nucleic acids may optionally be attached to one or more non-nucleotide moieties such as labels and other small molecules, large molecules (such as proteins, lipids, sugars, etc.), and solid or semi-solid supports, for example through covalent or non-covalent linkages with either the 5' or 3' end of the nucleic acid. Labels include any moiety that is detectable using any of a variety of detection methods known to those of skill in the art, and thus renders the attached oligonucleotide or nucleic acid similarly detectable. Some labels emit electromagnetic radiation that is optically detectable or visible. Alternately or in combination, some labels comprise a mass tag that renders the labeled oligonucleotide or nucleic acid visible in mass spectral data, or a redox tag that renders the labeled oligonucleotide or nucleic acid detectable by amperometry or voltametry. Some labels comprise a magnetic tag that facilitates separation and/or purification of the labeled oligonucleotide or nucleic acid. The nucleotide or polynucleotide is often not attached to a label, and the presence of the oligonucleotide or nucleic acid is directly detected.

Flow Cell Devices: Disclosed herein are flow devices that include a first reservoir housing a first solution and having an inlet end and an outlet end, wherein the first agent flows from the inlet end to the outlet end in the first reservoir; a second reservoir housing a second solution and having an inlet end and an outlet end, wherein the second agent flows from the inlet end to the outlet end in the second reservoir; a central region having an inlet end fluidically coupled to the outlet end of the first reservoir and the outlet end of the second reservoir through at least one valve. In the flow cell device, the volume of the first solution flowing from the outlet of the first reservoir to the inlet of the central region is less than the volume of the second solution flowing from the outlet of the second reservoir to the inlet of the central region.

The reservoirs described in the device can be used to house different reagents. In some aspects, the first solution housed in the first reservoir is different from the second solution that is housed in the second reservoir. The second solution comprises at least one reagent common to a plurality of reactions occurring in the central region. In some aspects, the second solution comprises at least one reagent selected from the list consisting of a solvent, a polymerase, and a dNTP. In some aspects, the second solution comprise low cost reagents. In some aspects, the first reservoir is fluidically coupled to the central region through a first valve and the second reservoir is fluidically coupled to the central region through a second valve. The valve can be a diaphragm valve or other suitable valves.

The design of the flow cell device can achieve a more efficient use of the reaction reagents than other sequencing device, particularly for costly reagents used in a variety of sequencing steps. In some aspects, the first solution comprises a reagent and the second solution comprises a reagent and the reagent in the first solution is more expensive than the reagent in the second solution. In some aspects, the first solution comprises a reaction-specific reagent and the second solution comprises nonspecific reagent common to all reaction occurring in the central region, and wherein the reaction specific reagent is more expensive than the nonspecific reagent. In some aspects, the first reservoir is positioned in close proximity to the inlet of the central region to reduce dead volume for delivery of the first solutions. In some aspects, the first reservoir is places closer to the inlet of the central region than the second reservoir. In some aspects, the reaction-specific reagent is configured in close proximity to the second diaphragm valve so as to reduce dead volume relative to delivery of the plurality of nonspecific reagents from the plurality of reservoirs to the first diaphragm valve.

Central Region: The central region can include a capillary tube or microfluidic chip having one or more microfluidic channels. In some embodiments, the capillary tube is an off-shelf product. The capillary tube or the microfluidic chip can also be removable from the device. In some embodiments, the capillary tube or microfluidic channel comprises an oligonucleotide population directed to sequence a eukaryotic genome. In some embodiments, the capillary tube or microfluidic channel in the central region can be removable.

Capillary flow cell devices: Disclosed herein are single capillary flow cell devices that comprise a single capillary and one or two fluidic adapters affixed to one or both ends of the capillary, where the capillary provides a fluid flow channel of specified cross-sectional area and length, and where the fluidic adapters are configured to mate with standard tubing to provide for convenient, interchangeable fluid connections with an external fluid flow control system.

FIG. 1 illustrates one non-limiting example of a single glass capillary flow cell device that comprises two fluidic adaptors—one affixed to each end of the piece of glass capillary—that are designed to mate with standard OD fluidic tubing. The fluidic adaptors can be attached to the capillary using any of a variety of techniques known to those of skill in the art including, but not limited to, press fit, adhesive bonding, solvent bonding, laser welding, etc., or any combination thereof.

In general, the capillary used in the disclosed flow cell devices (and flow cell cartridges to be described below) will have at least one internal, axially-aligned fluid flow channel (or "lumen") that runs the full length of the capillary. In some aspects, the capillary may have two, three, four, five, or more than five internal, axially-aligned fluid flow channels (or "lumen").

A number specified cross-sectional geometries for a single capillary (or lumen thereof) are consistent with the disclosure herein, including, but not limited to, circular, elliptical, square, rectangular, triangular, rounded square, rounded rectangular, or rounded triangular cross-sectional geometries. In some aspects, the single capillary (or lumen thereof) may have any specified cross-sectional dimension or set of dimensions. For example, in some aspects the largest cross-sectional dimension of the capillary lumen (e.g. the diameter if the lumen is circular in shape or the diagonal if the lumen is square or rectangular in shape) may range from about 10 µm to about 10 mm. In some aspects, the largest cross-sectional dimension of the capillary lumen may be at least 10 µm, at least 25 µm, at least 50 µm, at least 75 µm, at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In some aspects, the largest cross-sectional dimension of the capillary lumen may be at most 10 mm, at most 9 mm, at most 8 mm, at most 7 mm, at most 6 mm, at most 5 mm, at most 4 mm, at most 3 mm, at most 2 mm, at most 1 mm, at most 900 µm, at most 800 µm, at most 700 µm, at most 600 µm, at most 500 µm, at most 400 µm, at most 300 µm, at most 200 µm, at most 100 µm, at most 75 µm, at most 50 µm, at most 25 µm, or at most 10 µm. Any of the lower and upper values described in this paragraph may be combined to form a range included within the present disclosure, for example, in some aspects the largest cross-sectional dimension of the capillary lumen may range from about 100 µm to about 500 µm. Those of skill in the art will recognize that the largest cross-sectional dimension of the capillary lumen may have any value within this range, e.g., about 124 µm.

The length of the one or more capillaries used to fabricate the disclosed single capillary flow cell devices or flow cell cartridges may range from about 5 mm to about 5 cm or greater. In some instances, the length of the one or more capillaries may be less than 5 mm, at least 5 mm, at least 1 cm, at least 1.5 cm, at least 2 cm, at least 2.5 cm, at least 3 cm, at least 3.5 cm, at least 4 cm, at least 4.5 cm, or at least 5 cm. In some instances, the length of the one or more capillaries may be at most 5 cm, at most 4.5 cm, at most 4 cm, at most 3.5 cm, at most 3 cm, at most 2.5 cm, at most 2 cm, at most 1.5 cm, at most 1 cm, or at most 5 mm. Any of the lower and upper values described in this paragraph may be combined to form a range included within the present disclosure, for example, in some instances the length of the one or more capillaries may range from about 1.5 cm to about 2.5 cm. Those of skill in the art will recognize that the length of the one or more capillaries may have any value within this range, e.g., about 1.85 cm. In some instances, devices or cartridges may comprise a plurality of two or more capillaries that are the same length. In some instances, devices or cartridges may comprise a plurality of two or more capillaries that are of different lengths.

Capillaries in some cases have a gap height of about or exactly 50, 75, 100, 125, 150, 175, 200, 225, 250, 275, 300, 350, 400, or 500 um, or any value falling within the range defined thereby. Some preferred embodiments have gap heights of about 50 um-200 um, 50 um to 150 um, or comparable gap heights. The capillaries used for constructing the disclosed single capillary flow cell devices or capillary flow cell cartridges may be fabricated from any of a variety of materials known to those of skill in the art including, but not limited to, glass (e.g., borosilicate glass, soda lime glass, etc.), fused silica (quartz), polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) as more chemically inert alternatives. PEI is somewhere between polycarbonate and PEEK in terms of both cost and compatibility. FFKM is also known as Kalrez or any combination thereof.

The capillaries used for constructing the disclosed single capillary flow cell devices or capillary flow cell cartridges may be fabricated using any of a variety of techniques known to those of skill in the art, where the choice of fabrication technique is often dependent on the choice of material used, and vice versa. Examples of suitable capillary fabrication techniques include, but are not limited to, extrusion, drawing, precision computer numerical control (CNC) machining and boring, laser photoablation, and the like. Devices can be pour molded or injection molded to fabricate any three dimension structure for adapting to single piece flow cell.

Examples of commercial vendors that provide precision capillary tubing include Accu-Glass (St. Louis, Mo.; precision glass capillary tubing), Polymicro Technologies (Phoenix, Ariz.; precision glass and fused-silica capillary tubing), Friedrich & Dimmock, Inc. (Millville, N.J.; custom precision glass capillary tubing), and Drummond Scientific (Broomall, Pa.; OEM glass and plastic capillary tubing).

Microfluidic chip flow cell devices: Disclosed herein also include flow cell devices that comprise one or more microfluidic chips and one or two fluidic adapters affixed to one or both ends of the microfluidic chips, where the microfluidic chip provides one or more fluid flow channels of specified cross-sectional area and length, and where the fluidic adapters are configured to mate with the microfluidic chip to provide for convenient, interchangeable fluid connections with an external fluid flow control system.

A non-limiting example of a microfluidic chip flow cell device that comprises two fluidic adaptors—one affixed to each end of the microfluidic chip (e.g., the inlet of the microfluidic channels). The fluidic adaptors can be attached to the chip or channel using any of a variety of techniques known to those of skill in the art including, but not limited to, press fit, adhesive bonding, solvent bonding, laser welding, etc., or any combination thereof. In some instances, the inlet and/or outlet of the microfluidic channels on the chip are apertures on the top surface of the chip, and the fluidic adaptors can be attached or coupled to the inlet and outlet of the microfluidic chips.

When the central region comprises a microfluidic chip, the chip microfluidic chip used in the disclosed flow cell deices will have at least a single layer having one or more channels. In some aspects, the microfluidic chip has two layers bonded together to form one or more channels. In some aspects, the microfluidic chip can include three layers bonded together to form one or more channels. In some embodiments, the microfluidic channel has an open top. In some embodiments, the microfluidic channel is positioned between a top layer and a bottom layer.

In general, the microfluidic chip used in the disclosed flow cell devices (and flow cell cartridges to be described below) will have at least one internal, axially-aligned fluid flow channel (or "lumen") that runs the full length or a partial length of the chip. In some aspects, the microfluidic chip may have two, three, four, five, or more than five internal, axially-aligned microfluidic channels (or "lumen"). The microfluidic channel can be divided into a plurality of frames.

A number specified cross-sectional geometries for a single channels are consistent with the disclosure herein, including, but not limited to, circular, elliptical, square, rectangular, triangular, rounded square, rounded rectangular, or rounded triangular cross-sectional geometries. In some aspects, the channel may have any specified cross-sectional dimension or set of dimensions.

The microfluidic chip used for constructing the disclosed flow cell devices or flow cell cartridges may be fabricated from any of a variety of materials known to those of skill in the art including, but not limited to, glass (e.g., borosilicate glass, soda lime glass, etc.), quartz, polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) as more chemically inert alternatives. In some embodiments, the microfluidic chip comprises quartz. In some embodiments, the microfluidic chip comprises borosilicate glass.

The microfluidic chips used for constructing the described flow cell devices or flow cell cartridges may be fabricated using any of a variety of techniques known to those of skill in the art, where the choice of fabrication technique is often dependent on the choice of material used, and vice versa. The microfluidic channels on the chip can be constructed using techniques suitable for forming micro-structure or micro-pattern on the surface. In some aspects, the channel is formed by laser irradiation. In some aspects, the microfluidic channel is formed by focused femtosecond laser radiation. In some aspects, the microfluidic channel is formed by etching, including but not limited to chemical or laser etching.

When the microfluidic channels are formed on the microfluidic chip through etching, the microfluidic chip will comprise at least one etched layer. In some aspects, the microfluidic chip can include comprise one non-etched layer, and one non-etched layer, with the etched layer being bonded to the non-etched layer such that the non-etched layer forms a bottom layer or a cover layer for the channels. In some aspects, the microfluidic chip can include comprise one non-etched layer, and two non-etched layers, and wherein the etched layer is positioned between the two non-etched layers.

The chip described herein includes one or more microfluidic channels etched on the surface of the chip. The microfluidic channels are defined as fluid conduits with at least one minimum dimension from <1 nm to 1000 μm. The microfluidic channels can be fabricated through several different methods, such as laser radiation (e.g., femtosecond laser radiation), lithography, chemical etching, and any other suitable methods Channels on the chip surface can be created by selective patterning and plasma or chemical etching. The channels can be open, or they can be sealed by a conformal deposited film or layer on top to create subsurface or buried channels in the chip. In some embodiments, the channels are created from the removal of a sacrificial layer on the chip. This method does not require the bulk wafer to be etched away. Instead, the channel is located on the surface of the wafer. Examples of direct lithography include electron beam direct-write and focused ion beam milling.

The microfluidic channel system is coupled with an imaging system to capture or detect signals of DNA bases. The microfluidic channel system, fabricated on either a glass or silicon substrate, has channel heights and widths on the order of <1 nm to 1000 μm. For example, in some embodiments a channel may have a depth of 1-50 μm, 1-100 μm, 1-150 μm, 1-200 μm, 1-250 μm, 1-300 μm, 50-100 μm, 50-200 μm, or 50-300 μm, or greater than 300 μm, or a range defined by any two of these values. In some embodiments, a channel may have a depth of 3 mm or more. In some embodiments, a channel may have a depth of 30 mm or more. In some embodiments, a channel may have a length of less than 0.1 mm, between 0.1 mm and 0.5 mm, between 0.1 mm and 1 mm, between 0.1 mm and 5 mm, between 0.1 mm and 10 mm, between 0.1 mm and 25 mm, between 0.1 mm and 50 mm, between 0.1 mm and 100 mm, between 0.1 mm and 150 mm, between 0.1 mm and 200 mm, between 0.1 mm and 250 mm, between 1 mm and 5 mm, between 1 mm and 10 mm, between 1 mm and 25 mm, between 1 mm and 50 mm, between 1 mm and 100 mm, between 1 mm and 150 mm, between 1 mm and 200 mm, between 1 mm and 250 mm, between 5 mm and 10 mm, between 5 mm and 25 mm, between 5 mm and 50 mm, between 5 mm and 100 mm, between 5 mm and 150 mm, between 5 mm and 200 mm, between 1 mm and 250 mm, or greater than 250 mm, or a range defined by any two of these values. In some embodiments, a channel may have a length of 2 m or more. In some embodiments, a channel may have a length of 20 m or more. In some embodiments, a channel may have a width of less than 0.1 mm, between 0.1 mm and 0.5 mm, between 0.1 mm and 1 mm, between 0.1 mm and 5 mm, between 0.1 mm and 10 mm, between 0.1 mm and 15 mm, between 0.1 mm and 20 mm, between 0.1 mm and 25 mm, between 0.1 mm and 30 mm, between 0.1 mm and 50 mm, or greater than 50 mm, or a range defined by any two of these values. In some embodiments, a channel may have a width of 500 mm or more. In some embodiments, a channel may have a width of 5 m or more. The channel length can be in the micrometer range.

The one or more materials used to fabricate the capillaries or microfluidic chips for the disclosed devices are often optically transparent to facilitate use with spectroscopic or imaging-based detection techniques. The entire capillary will be optically transparent. Alternately, only a portion of the capillary (e.g., an optically transparent "window") will be optically transparent. In some instances, the entire microfluidic chip will be optically transparent. In some instances, only a portion of the microfluidic chip (e.g., an optically transparent "window") will be optically transparent.

As noted above, the fluidic adapters that are attached to the capillaries or microfluidic channels of the flow cell devices and cartridges disclosed herein are designed to mate with standard OD polymer or glass fluidic tubing or microfluidic channel. As illustrated in FIG. 1, one end of the fluidic adapter may be designed to mate to capillary having specific dimensions and cross-sectional geometry, while the other end may be designed to mate with fluidic tubing having the same or different dimensions and cross-sectional geometry. The adapters may be fabricated using any of a variety of suitable techniques (e.g., extrusion molding, injection molding, compression molding, precision CNC machining, etc.) and materials (e.g., glass, fused-silica, ceramic, metal, polydimethylsiloxane, polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), etc.), where the choice of fabrication technique is often dependent on the choice of material used, and vice versa.

Surface coatings: An interior surface (or surface of a capillary lumen) of one or more capillaries or the channel on the microfluidic chip is often coated using any of a variety of surface modification techniques or polymer coatings known to those of skill in the art.

Examples of suitable surface modification or coating techniques include, but are not limited to, the use of silane chemistries (e.g., aminopropyltrimethoxysilane (APTMS), aminopropyltriethoxysilane (APTES), triethoxysilane, diethoxydimethylsilane, and other linear, branched, or cyclic silanes) for covalent attachment of functional groups or molecules to capillary lumen surfaces, covalently or non-covalently attached polymer layers (e.g., layers of streptavidin, polyacrilamide, polyester, dextran, poly-lysine, poly-acrylamide/poly-lysine copolymers, polyethylene glycol (PEG), poly (n-isopropylacrylamide) (PNIPAM), poly(2-hydroxyethyl methacrylate), (PHEMA), poly(oligo(ethylene glycol) methyl ether methacrylate (POEGMA), polyacrylic acid (PAA), poly(vinylpyridine), poly(vinylimidazole) and poly-lysine copolymers), or any combination thereof.

Examples of conjugation chemistries that may be used to graft one or more layers of material (e.g. polymer layers) to the support surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane chemistries.

The number of layers of polymer or other chemical layers on the interior or lumen surface may range from 1 to about 10 or greater than 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, all of the layers may comprise the same material. In some instances, each layer may comprise a different material. In some instances, the plurality of layers may comprise a plurality of materials.

In a preferred aspect, one or more layers of a coating material may be applied to the capillary lumen surface or the interior surface of the channel on the microfluidic chip, where the number of layers and/or the material composition of each layer is chosen to adjust one or more surface properties of the capillary or channel lumen, as noted in U.S. patent application Ser. No. 16/363,842.

Examples of surface properties that may be adjusted include, but are not limited to, surface hydrophilicity/hydrophobicity, overall coating thickness, the surface density of chemically-reactive functional groups, the surface density of grafted linker molecules or oligonucleotide primers, etc. In some preferred applications, one or more surface properties of the capillary or channel lumen are adjusted to, for example, (i) provide for very low non-specific binding of proteins, oligonucleotides, fluorophores, and other molecular components of chemical or biological analysis applications, including solid-phase nucleic acid amplification and/or sequencing applications, (ii) provide for improved solid-phase nucleic acid hybridization specificity and efficiency, and (iii) provide for improved solid-phase nucleic acid amplification rate, specificity, and efficiency.

One or more surface modification and/or polymer layers may be applied by flowing one or more appropriate chemical coupling or coating reagents through the capillaries or channel prior to use for their intended application. One or more coating reagents may be added to a buffer used, e.g., a nucleic acid hybridization, amplification reaction, and/or sequencing reaction to provide for dynamic coating of the capillary lumen surface.

Low non-specific binding surface: The interior surface of the channel and capillary tube described herein can be grafted or coated with a composition comprising low non-specific binding surface compositions that enable improved nucleic acid hybridization and amplification performance.

In some instances, fluorescence images of the disclosed low non-specific binding surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

In order to scale primer surface density and add additional dimensionality to hydrophilic or amphoteric surfaces, substrates comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some instances, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some instances, high primer density materials may be constructed in solution and subsequently layered onto the surface in multiple steps.

Those of skill in the art will realize that a given hydrophilic, low-binding support surface of the present disclosure may exhibit a water contact angle having a value of anywhere less than 50 degrees.

The disclosed interior surface of the channel and capillary may comprise a substrate (or support structure), one or more layers of a covalently or non-covalently attached low-binding, chemical modification layers, e.g., silane layers, polymer films, and one or more covalently or non-covalently attached primer sequences that may be used for tethering single-stranded template oligonucleotides to the support surface. In some instances, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. Often, the formulation of the surface may be varied such that non-specific hybridization on the support surface is minimized or reduced relative to a comparable monolayer. The formulation of the surface may be varied such that non-specific amplification on the support surface is minimized or reduced relative to a comparable monolayer. The formulation of the surface may be varied such that specific amplification rates and/or yields on the support surface are maximized. Amplification levels suitable for detection are achieved in no more than 2, 3, 4, 5, 6, 7, 8, 9, 10, 15, 20, 25, 30, or more than 30 amplification cycles in some cases disclosed herein.

Examples of materials from which the substrate or support structure may be fabricated include, but are not limited to, glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The substrate or support structure may be rendered in any of a variety of geometries and dimensions known to those of skill in the art, and may comprise any of a variety of materials known to those of skill in the art. For example, in some instances the substrate or support structure may be locally planar (e.g., comprising a microscope slide or the surface of a microscope slide). Globally, the substrate or support structure may be cylindrical (e.g., comprising a capillary or the interior surface of a capillary), spherical (e.g., comprising the outer surface of a non-porous bead), or irregular (e.g., comprising the outer surface of an irregularly-shaped, non-porous bead or particle). In some instances, the surface of the substrate or support structure used for nucleic acid hybridization and amplification may be a solid, non-porous surface. In some instances, the surface of the substrate or support structure used for nucleic acid hybridization and amplification may be porous, such that the coatings described herein penetrate the porous surface, and nucleic acid hybridization and amplification reactions performed thereon may occur within the pores.

The substrate or support structure that comprises the one or more chemically-modified layers, e.g., layers of a low non-specific binding polymer, may be independent or integrated into another structure or assembly. For example, in some instances, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some preferred embodiments, the substrate or support structure comprises the interior surface (such as the lumen surface) of a capillary. In alternate preferred embodiments the substrate or support structure comprises the interior surface (such as the lumen surface) of a capillary etched into a planar chip.

The chemical modification layers may be applied uniformly across the surface of the substrate or support structure. Alternately, the surface of the substrate or support structure may be non-uniformly distributed or patterned, such that the chemical modification layers are confined to one or more discrete regions of the substrate. For example, the substrate surface may be patterned using photolithographic techniques to create an ordered array or random pattern of chemically-modified regions on the surface. Alternately or in combination, the substrate surface may be patterned using, e.g., contact printing and/or ink jet printing techniques. In some instances, an ordered array or random patter of chemically-modified discrete regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions, or any intermediate number spanned by the range herein.

In order to achieve low nonspecific binding surfaces (also referred to herein as "low binding" or "passivated" surfaces), hydrophilic polymers may be nonspecifically adsorbed or covalently grafted to the substrate or support surface. Typically, passivation is performed utilizing poly (ethylene glycol) (PEG, also known as polyethylene oxide (PEO) or polyoxyethylene), poly(vinyl alcohol) (PVA), poly (vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(-hydroxylethyl methacrylate) (PHEMA), poly(oligo (ethylene glycol) methyl ether methacrylate) (POEGMA), polyglutamic acid (PGA), poly-lysine, poly-glucoside, streptavidin, dextran, or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some instances, two or more layers of a hydrophilic polymer, e.g., a linear polymer, branched polymer, or multi-branched polymer, may be deposited on the surface. In some instances, two or more layers may be covalently coupled to each other or internally cross-linked to improve the stability of the resulting surface. In some instances, oligonucleotide primers with different base sequences and base modifications (or other biomolecules, e.g., enzymes or antibodies) may be tethered to the resulting surface layer at various surface densities. In some instances, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

In some embodiments, the hydrophilic polymer can be a cross linked polymer. In some embodiments, the cross-linked polymer can include one type of polymer cross linked with another type of polymer. Examples of the crossed-linked polymer can include poly(ethylene glycol) cross-linked with another polymer selected from polyethylene oxide (PEO) or polyoxyethylene), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(-hydroxylethyl methacrylate) (PHEMA), poly(oligo (ethylene glycol) methyl ether methacrylate) (POEGMA), polyglutamic acid (PGA), poly-lysine, poly-glucoside, streptavidin, dextran, or other hydrophilic polymers. In some embodiments, the cross-linked polymer can be a poly(ethylene glycol) cross-linked with polyacrylamide.

The interior surface of one or more capillaries or the channels on the microfluidic chip or wall of the capillary can exhibit low non-specific binding of proteins and other amplification reaction reagents or components, and improved stability to repetitive exposure to different solvents, changes in temperature, chemical affronts such as low pH, or long term storage.

The disclosed low non-specific binding supports comprising one or more polymer coatings, e.g., PEG polymer films, that minimize non-specific binding of protein and labeled nucleotides to the solid support. The subsequent demonstration of improved nucleic acid hybridization and amplification rates and specificity may be achieved through one or more of the following additional aspects of the present disclosure: (i) primer design (sequence and/or modifications), (ii) control of tethered primer density on the solid support, (iii) the surface composition of the solid support, (iv) the surface polymer density of the solid support, (v) the use of improved hybridization conditions before and during amplification, and/or (vi) the use of improved amplification formulations that decrease non-specific primer amplification or increase template amplification efficiency.

The advantages of the disclosed low non-specific binding supports and associated hybridization and amplification methods confer one or more of the following additional advantages for any sequencing system: (i) decreased fluidic wash times (due to reduced non-specific binding, and thus faster sequencing cycle times), (ii) decreased imaging times (and thus faster turnaround times for assay readout and sequencing cycles), (iii) decreased overall work flow time requirements (due to decreased cycle times), (iv) decreased detection instrumentation costs (due to the improvements in CNR), (v) improved readout (base-calling) accuracy (due to improvements in CNR), (vi) improved reagent stability and decreased reagent usage requirements (and thus reduced reagents costs), and (vii) fewer run-time failures due to nucleic acid amplification failures.

The low binding hydrophilic surfaces (multilayer and/or monolayer) for surface bioassays, e.g., genotyping and sequencing assays, are created by using any combination of the following. In some embodiments, genotyping assays are performed. In these embodiments, the interior surface of the flow cell device is coated with at least one oligonucleotide or nucleic acid molecule type. In certain instances, a plurality of each oligonucleotide molecule type is located within at least one discrete and spatially indexed region of the surface, where it is immobilized. Each oligonucleotide molecule type, or probe type, may comprise a locus-specific primer or an allele specific primer. In certain instances, the array of oligonucleotide molecule types, each at discrete and spatially indexed regions is contacted with a mixture comprising different nucleic acid template types, also known as targets, and a polymerase to form a complex. In some instances, the nucleic acid template is associated with a fluorescent label. In some instances, the fluorescent label is conjugated to a polymeric core, wherein the labeled core can be associated with a nucleic acid template type. A non-covalent bond may be used to associate the labeled polymeric core to the nucleic acid template. After contacting the surface, the mixture is washed away, replaced by another solution and imaged with a fluorescence imager. When positive matches are made between the surface immobilized locus or allele containing probes and the complimentary nucleic acid template, the discrete region may exhibit a fluorescence signal above the background. In certain instances, each discrete region exhibiting a probe-target match is identified by the emission of fluorescence and compared to the background. In certain instances, the contrast to noise ratio (CNR) achieves values greater than 20. Positive matches between the discrete and spatially indexed locations may therefore identify the presence of specific loci or alleles present in the multiplexed sample from which the nucleic acid template is generated.

Polar protic, polar aprotic and/or nonpolar solvents for depositing and/or coupling linear or multi-branched hydrophilic polymer subunits on a substrate surface. Some multi-branched hydrophilic polymer subunits may contain functional end groups to promote covalent coupling or non-covalent binding interactions with other polymer subunits. Examples of suitable functional end groups include biotin, methoxy ether, carboxylate, amine, ester compounds, azide, alkyne, maleimide, thiol, and silane groups.

Any combination of linear, branched, or multi-branched polymer subunits coupled through subsequent layered addition via modified coupling chemistry/solvent/buffering systems that may include individual subunits with orthogonal end coupling chemistries or any of the respective combinations, such that resultant surface is hydrophilic and exhibits low nonspecific binding of proteins and other molecular assay components. In some instances, the hydrophilic, functionalized substrate surfaces of the present disclosure exhibit contact angle measurements that do not exceed 35 degrees.

Subsequent biomolecule attachment (e.g., of proteins, peptides, nucleic acids, oligonucleotides, or cells) on the low binding/hydrophilic substrates via any of a variety of individual conjugation chemistries to be described below, or any combination thereof. Layer deposition and/or conjugation reactions may be performed using solvent mixtures which may contain any ratio of the following components: ethanol, methanol, acetonitrile, acetone, DMSO, DMF, $H_2O$, and the like. In addition, compatible buffering systems in the desirable pH range of 5-10 may be used for controlling the rate and efficiency of deposition and coupling, whereby coupling rates is excess of >5× of those for conventional aqueous buffer-based methods may be achieved.

The disclosed low non-specific binding supports and associated nucleic acid hybridization and amplification methods may be used for the analysis of nucleic acid molecules derived from any of a variety of different cell, tissue, or sample types known to those of skill in the art. For example, nucleic acids may be extracted from cells, or tissue samples comprising one or more types of cells, derived from eukaryotes (such as animals, plants, fungi, protista), archaebacteria, or eubacteria. In some cases, nucleic acids may be extracted from prokaryotic or eukaryotic cells, such as adherent or non-adherent eukaryotic cells. Nucleic acids are variously extracted from, for example, primary or immortalized rodent, porcine, feline, canine, bovine, equine, primate, or human cell lines. Nucleic acids may be extracted from any of a variety of different cell, organ, or tissue types (e.g., white blood cells, red blood cells, platelets, epithelial cells, endothelial cells, neurons, glial cells, astrocytes, fibroblasts, skeletal muscle cells, smooth muscle cells, gametes, or cells from the heart, lungs, brain, liver, kidney, spleen, pancreas, thymus, bladder, stomach, colon, or small intestine). Nucleic acids may be extracted from normal or healthy cells. Alternately or in combination, acids are extracted from diseased cells, such as cancerous cells, or from pathogenic cells that are infecting a host. Some nucleic acids may be extracted from a distinct subset of cell types, e.g., immune cells (such as T cells, cytotoxic (killer) T cells, helper T cells, alpha beta T cells, gamma delta T cells, T cell progenitors, B cells, B-cell progenitors, lymphoid stem cells, myeloid progenitor cells, lymphocytes, granulocytes, Natural Killer cells, plasma cells, memory cells, neutrophils, eosinophils, basophils, mast cells, monocytes, dendritic cells, and/or macrophages, or any combination thereof), undifferentiated human stem cells, human stem cells that have been induced to differentiate, rare cells (e.g., circulating tumor cells (CTCs), circulating epithelial cells, circulating endothelial cells, circulating endometrial cells, bone marrow cells, progenitor cells, foam cells, mesenchymal cells, or trophoblasts). Other cells are contemplated and consistent with the disclosure herein.

As a result of the surface passivation techniques disclosed herein, proteins, nucleic acids, and other biomolecules do not "stick" to the substrates, that is, they exhibit low nonspecific binding (NSB). Examples are shown below using standard monolayer surface preparations with varying glass preparation conditions. Hydrophilic surface that have been passivated to achieve ultra-low NSB for proteins and nucleic acids require novel reaction conditions to improve primer deposition reaction efficiencies, hybridization performance, and induce effective amplification. All of these processes require oligonucleotide attachment and subsequent protein binding and delivery to a low binding surface. As described below, the combination of a new primer surface conjugation formulation (Cy3 oligonucleotide graft titration) and resulting ultra-low non-specific background (NSB functional tests performed using red and green fluorescent dyes) yielded results that demonstrate the viability of the disclosed approaches. Some surfaces disclosed herein exhibit a ratio of specific (e.g., hybridization to a tethered primer or probe) to nonspecific binding (e.g., $B_{inter}$) of a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein. Some surfaces disclosed herein exhibit a ratio of specific to nonspecific fluorescence signal (e.g., for specifically-hybridized to nonspecifically bound labeled oligonucleotides, or for specifically-amplified to nonspecifically-bound (Banter) or non-specifically amplified (Bra) labeled oligonucleotides or a combination thereof $(Ba_{nter}a))+B$ for a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein.

Grafting low non-specific binding layer: The attachment chemistry used to graft a first chemically-modified layer to an interior surface of the flow cell (capillary or channel) will generally be dependent on both the material from which the support is fabricated and the chemical nature of the layer. In some instances, the first layer may be covalently attached to the support surface. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the support surface. For example, glass or silicon surfaces may be acid-washed using a Piranha solution (a mixture of sulfuric acid ($H_2SO_4$) and hydrogen peroxide ($H_2O_2$)) and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding support surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Any of a variety of molecules known to those of skill in the art including, but not limited to, amino acids, peptides, nucleotides, oligonucleotides, other monomers or polymers, or combinations thereof may be used in creating the one or more chemically-modified layers on the support surface, where the choice of components used may be varied to alter one or more properties of the support surface, e.g., the surface density of functional groups and/or tethered oligonucleotide primers, the hydrophilicity/hydrophobicity of the support surface, or the three three-dimensional nature (i.e., "thickness") of the support surface. Examples of preferred polymers that may be used to create one or more layers of low non-specific binding material in any of the disclosed support surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the support surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (-hydroxylethyl methacrylate) (branced PHEMA), branched poly(oligo(ethylene glycol) methyl ether methacrylate)

(branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches. Molecules often exhibit a 'power of 2' number of branches, such as 2, 4, 8, 16, 32, 64, or 128 branches.

Exemplary PEG multilayers include PEG (8 arm, 16 arm, 8 arm) on PEG-amine-APTES. Similar concentrations were observed for 3-layer multi-arm PEG (8 arm, 16 arm, 8 arm) and (8 arm, 64 arm, 8 arm) on PEG-amine-APTES exposed to 8 uM primer, and 3-layer multi-arm PEG (8 arm, 8 arm, 8 arm) using star-shape PEG-amine to replace 16 arm and 64 arm. PEG multilayers having comparable first, second and third PEG layers are also contemplated.

Linear, branched, or multi-branched polymers used to create one or more layers of any of the multi-layered surfaces disclosed herein may have a molecular weight of at least 500, at least 1,000, at least 1,500, at least 2,000, at least 2,500, at least 3,000, at least 3,500, at least 4,000, at least 4,500, at least 5,000, at least 7,500, at least 10,000, at least 12,500, at least 15,000, at least 17,500, at least 20,000, at least 25,000, at least 30,000, at least 35,000, at least 40,000, at least 45,000, or at least 50,000 Daltons. In some instances, the linear, branched, or multi-branched polymers used to create one or more layers of any of the multi-layered surfaces disclosed herein may have a molecular weight of at most 50,000, at most 45,000, at most 40,000, at most 35,000, at most 30,000, at most 25,000, at most 20,000, at most 17,500, at most 15,000, at most 12,500, at most 10,000, at most 7,500, at most 5,000, at most 4,500, at most 4,000, at most 3,500, at most 3,000, at most 2,500, at most 2,000, at most 1,500, at most 1,000, or at most 500 Daltons. Any of the lower and upper values described in this paragraph may be combined to form a range included within the present disclosure, for example, in some instances the molecular weight of linear, branched, or multi-branched polymers used to create one or more layers of any of the multi-layered surfaces disclosed herein may range from about 1,500 to about 20,000 Daltons. Those of skill in the art will recognize that the molecular weight of linear, branched, or multi-branched polymers used to create one or more layers of any of the multi-layered surfaces disclosed herein may have any value within this range, e.g., about 1,260 Daltons.

In some instances, e.g., wherein at least one layer of a multi-layered surface comprises a branched polymer, the number of covalent bonds between a branched polymer molecule of the layer being deposited and molecules of the previous layer may range from about one covalent linkages per molecule and about 32 covalent linkages per molecule. In some instances, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32, or more than 32 covalent linkages per molecule. In some instances, the number of covalent bonds between a branched polymer molecule of the new layer and molecules of the previous layer may be at most 32, at most 30, at most 28, at most 26, at most 24, at most 22, at most 20, at most 18, at most 16, at most 14, at most 12, at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of covalent bonds between a branched polymer molecule of the new layer and molecules of the previous layer may range from about 4 to about 16. Those of skill in the art will recognize that the number of covalent bonds between a branched polymer molecule of the new layer and molecules of the previous layer may have any value within this range, e.g., about 11 in some instances, or an average number of about 4.6 in other instances.

Any reactive functional groups that remain following the coupling of a material layer to the support surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface of the disclosed low binding supports may range from 1 to about 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, all of the layers may comprise the same material. In some instances, each layer may comprise a different material. In some instances, the plurality of layers may comprise a plurality of materials. In some instances at least one layer may comprise a branched polymer. In some instance, all of the layers may comprise a branched polymer.

One or more layers of low non-specific binding material may in some cases be deposited on and/or conjugated to the substrate surface using a polar protic solvent, a polar aprotic solvent, a nonpolar solvent, or any combination thereof. In some instances the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some instances, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of water or an aqueous buffer solution. In some instances, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of an organic solvent. The pH of the solvent mixture used may be less than 5, 5, 5, 5, 6, 6, 6.5, 7, 7.5, 8, 8.5, 9, 9.5, 10, or greater than 10, or any value spanned or adjacent to the range described herein.

In some instances, one or more layers of low non-specific binding material may be deposited on and/or conjugated to the substrate surface using a mixture of organic solvents, wherein the dielectric constant of at least once component is less than 40 and constitutes at least 50% of the total mixture by volume. In some instances, the dielectric constant of the at least one component may be less than 10, less than 20, less than 30, less than 40. In some instances, the at least one component constitutes at least 20%, at least 30%, at least 40%, at least 50%, at least 50%, at least 60%, at least 70%, or at least 80% of the total mixture by volume.

As noted, the low non-specific binding supports of the present disclosure exhibit reduced non-specific binding of proteins, nucleic acids, and other components of the hybridization and/or amplification formulation used for solid-phase nucleic acid amplification. The degree of non-specific binding exhibited by a given support surface may be assessed either qualitatively or quantitatively. For example, in some instances, exposure of the surface to fluorescent dyes (e.g., Cy3, Cy5, etc.), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some instances, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under conditions where fluorescence signal is linearly related (or related in a predictable manner) to the number of fluorophores on the support surface (e.g., under conditions where signal saturation and/or self-quenching of the fluorophore is not an issue) and suitable calibration standards are used. In some instances, other techniques known to those of skill in the art, for example, radioisotope labeling and counting methods may be used for quantitative assessment of the degree to which non-specific binding is exhibited by the different support surface formulations of the present disclosure.

Some surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to nonspecific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some instances, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label known to one of skill in the art. In some instances, the degree of non-specific binding exhibited by a given support surface formulation may thus be assessed in terms of the number of non-specifically bound protein molecules (or other molecules) per unit area. In some instances, the low-binding supports of the present disclosure may exhibit non-specific protein binding (or non-specific binding of other specified molecules, e.g., Cy3 dye) of less than 0.001 molecule per $\mu m^2$, less than 0.01 molecule per $\mu m^2$, less than 0.1 molecule per $\mu m^2$, less than 0.25 molecule per $\mu m^2$, less than 0.5 molecule per $\mu m^2$, less than 1 molecule per $\mu m^2$, less than 10 molecules per $\mu m^2$, less than 100 molecules per $\mu m^2$, or less than 1,000 molecules per $\mu m^2$. Those of skill in the art will realize that a given support surface of the present disclosure may exhibit non-specific binding falling anywhere within this range, for example, of less than 86 molecules per $\mu m^2$. For example, some modified surfaces disclosed herein exhibit nonspecific protein binding of less than 0.5 molecule/um$^2$ following contact with a 1 uM solution of Cy3 labeled streptavidin (GE Amersham) in phosphate buffered saline (PBS) buffer for 15 minutes, followed by 3 rinses with deionized water. Some modified surfaces disclosed herein exhibit nonspecific binding of Cy3 dye molecules of less than 2 molecules per um$^2$. In independent nonspecific binding assays, 1 uM labeled Cy3 SA (ThermoFisher), 1 uM Cy5 SA dye (ThermoFisher), 10 uM Aminoallyl-dUTP-ATTO-647N (Jena Biosciences), 10 uM Aminoallyl-dUTP-ATTO-Rho11 (Jena Biosciences), 10 uM Aminoallyl-dUTP-ATTO-Rho11 (Jena Biosciences), 10 uM 7-Propargylamino-7-deaza-dGTP-Cy5 (Jena Biosciences, and 10 uM 7-Propargylamino-7-deaza-dGTP-Cy3 (Jena Biosciences) were incubated on the low binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon (GE Healthcare Lifesciences, Pittsburgh, Pa.) instrument using the Cy3, AF555, or Cy5 filter sets (according to dye test performed) as specified by the manufacturer at a PMT gain setting of 800 and resolution of 50-100 µm. For higher resolution imaging, images were collected on an Olympus IX83 microscope (Olympus Corp., Center Valley, Pa.) with a total internal reflectance fluorescence (TIRF) objective (20×, 0.75 NA or 100×, 1.5 NA, Olympus), an sCMOS Andor camera (Zyla 4.2. Dichroic mirrors were purchased from Semrock (IDEX Health & Science, LLC, Rochester, N.Y.), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per $\mu m^2$.

In some instances, the surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some instances, the surfaces disclosed herein exhibit a ratio of specific to nonspecific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

The low-background surfaces consistent with the disclosure herein may exhibit specific dye attachment (e.g., Cy3 attachment) to non-specific dye adsorption (e.g., Cy3 dye adsorption) ratios of at least 3:1, 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 3:1, 4:1, 5:1, 6:1, 7:1, 8:1, 9:1, 10:1, 15:1, 20:1, 30:1, 40:1, 50:1, or more than 50:1.

In some instances, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding support surfaced disclosed herein may range from about 0 degrees to about 50 degrees. In some instances, the water contact angle for the hydrophilic, low-binding support surfaced disclosed herein may no more than 50 degrees, 45 degrees, 40 degrees, 35 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than any value within this range, e.g., no more than 40 degrees. Those of skill in the art will realize that a given hydrophilic, low-binding support surface of the present disclosure may exhibit a water contact angle having a value of anywhere within this range, e.g., about 27 degrees.

In some instances, the hydrophilic surfaces disclosed herein facilitate reduced wash times for bioassays, often due to reduced nonspecific binding of biomolecules to the low-binding surfaces. In some instances, adequate wash steps may be performed in less than 60, 50, 40, 30, 20, 15, 10, or less than 10 seconds. For example, in some instances adequate wash steps may be performed in less than 30 seconds.

Oligonucleotide primers and adapter sequences: In general, at least one layer of the one or more layers of low non-specific binding material may comprise functional groups for covalently or non-covalently attaching oligonucleotide molecules, e.g., adapter or primer sequences, or the at least one layer may already comprise covalently or non-covalently attached oligonucleotide adapter or primer sequences at the time that it is deposited on the support surface. In some instances, the oligonucleotides tethered to the polymer molecules of at least one third layer may be distributed at a plurality of depths throughout the layer.

In some instances, the oligonucleotide adapter or primer molecules are covalently coupled to the polymer in solution, i.e., prior to coupling or depositing the polymer on the surface. In some instances, the oligonucleotide adapter or primer molecules are covalently coupled to the polymer after it has been coupled to or deposited on the surface. In some instances, at least one hydrophilic polymer layer comprises a plurality of covalently-attached oligonucleotide adapter or primer molecules. In some instances, at least two, at least three, at least four, or at least five layers of hydrophilic polymer comprise a plurality of covalently-attached adapter or primer molecules.

In some instances, the oligonucleotide adapter or primer molecules may be coupled to the one or more layers of hydrophilic polymer using any of a variety of suitable conjugation chemistries known to those of skill in the art. For example, the oligonucleotide adapter or primer sequences may comprise moieties that are reactive with amine groups, carboxyl groups, thiol groups, and the like. Examples of suitable amine-reactive conjugation chemistries that may be used include, but are not limited to, reactions involving isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester groups. Examples of suitable carboxyl-reactive conjugation chemistries include, but are not limited to, reactions involving carbodiimide compounds, e.g., water soluble EDC (1-ethyl-3-(3-dimethylaminopropyl)carbodiimide.HCL). Examples of suitable sulfydryl-reactive conjugation chemistries include maleimides, haloacetyls and pyridyl disulfides.

One or more types of oligonucleotide molecules may be attached or tethered to the support surface. In some instances, the one or more types of oligonucleotide adapters or primers may comprise spacer sequences, adapter sequences for hybridization to adapter-ligated template library nucleic acid sequences, forward amplification primers, reverse amplification primers, sequencing primers, and/or molecular barcoding sequences, or any combination thereof. In some instances, 1 primer or adapter sequence may be tethered to at least one layer of the surface. In some instances, at least 2, 3, 4, 5, 6, 7, 8, 9, 10, or more than 10 different primer or adapter sequences may be tethered to at least one layer of the surface.

In some instances, the tethered oligonucleotide adapter and/or primer sequences may range in length from about 10 nucleotides to about 100 nucleotides. In some instances, the tethered oligonucleotide adapter and/or primer sequences may be at least 10, at least 20, at least 30, at least 40, at least 50, at least 60, at least 70, at least 80, at least 90, or at least 100 nucleotides in length. In some instances, the tethered oligonucleotide adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered oligonucleotide adapter and/or primer sequences may range from about 20 nucleotides to about 80 nucleotides. Those of skill in the art will recognize that the length of the tethered oligonucleotide adapter and/or primer sequences may have any value within this range, e.g., about 24 nucleotides.

In some instances, the tethered adapter or primer sequences may comprise modifications designed to facilitate the specificity and efficiency of nucleic acid amplification as performed on the low-binding supports. For example, in some instances the primer may comprise polymerase stop points such that the stretch of primer sequence between the surface conjugation point and the modification site is always in single-stranded form and functions as a loading site for 5' to 3' helicases in some helicase-dependent isothermal amplification methods. Other examples of primer modifications that may be used to create polymerase stop points include, but are not limited to, an insertion of a PEG chain into the backbone of the primer between two nucleotides towards the 5' end, insertion of an abasic nucleotide (i.e., a nucleotide that has neither a purine nor a pyrimidine base), or a lesion site which can be bypassed by the helicase.

As will be discussed further in the examples below, it may be desirable to vary the surface density of tethered oligonucleotide adapters or primers on the support surface and/or the spacing of the tethered adapter or primers away from the support surface (e.g., by varying the length of a linker molecule used to tether the adapter or primers to the surface) in order to "tune" the support for optimal performance when using a given amplification method. As noted below, adjusting the surface density of tethered oligonucleotide adapters or primers may impact the level of specific and/or non-specific amplification observed on the support in a manner that varies according to the amplification method selected. In some instances, the surface density of tethered oligonucleotide adapters or primers may be varied by adjusting the ratio of molecular components used to create the support surface. For example, in the case that an oligonucleotide primer—PEG conjugate is used to create the final layer of a low-binding support, the ratio of the oligonucleotide primer—PEG conjugate to a non-conjugated PEG molecule may be varied. The resulting surface density of tethered primer molecules may then be estimated or measured using any of a variety of techniques known to those of skill in the art. Examples include, but are not limited to, the use of radioisotope labeling and counting methods, covalent coupling of a cleavable molecule that comprises an optically-detectable tag (e.g., a fluorescent tag) that may be cleaved from a support surface of defined area, collected in a fixed volume of an appropriate solvent, and then quantified by comparison of fluorescence signals to that for a calibration solution of known optical tag concentration, or using fluorescence imaging techniques provided that care has been taken with the labeling reaction conditions and image acquisition settings to ensure that the fluorescence signals are linearly related to the number of fluorophores on the surface (e.g., that there is no significant self-quenching of the fluorophores on the surface).

In some instances, the resultant surface density of oligonucleotide adapters or primers on the low binding support surfaces of the present disclosure may range from about 100 primer molecules per $\mu m^2$ to about 1,000,000 primer molecules per $\mu m^2$. In some instances, the surface density of oligonucleotide adapters or primers may be at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per $\mu m^2$. In some instances, the surface density of oligonucleotide adapters or primers may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, or at most 100 molecules per $\mu m^2$. Any of the lower and upper values described in this paragraph may be combined to form a range included within the present disclosure, for example, in some instances the surface density of adapters or primers may range from about 10,000 molecules per $\mu m^2$ to about 100,000 molecules per $\mu m^2$. Those of skill in the art will recognize that the surface density of adapter or primer molecules may have any value within this range, e.g., about 3,800 molecules per $\mu m^2$ in some instances, or about 455,000 molecules per $\mu m^2$ in other instances. In some instances, as will be discussed further below, the surface density of template library nucleic acid sequences (e.g., sample DNA molecules) initially hybridized to adapter or primer sequences on the support surface may be less than or equal to that indicated for the surface density of tethered oligonucleotide primers. In some instances, as will also be discussed further below, the surface density of clonally-amplified template library nucleic acid sequences hybridized to adapter or primer sequences on the support surface may span the same range or a different range as that indicated for the surface density of tethered oligonucleotide adapters or primers.

Local surface densities of adapter or primer molecules as listed above do not preclude variation in density across a surface, such that a surface may comprise a region having an oligo density of, for example, 500,000/$um^2$, while also comprising at least a second region having a substantially different local density.

Hybridization of nucleic acid molecules to low-binding supports: In some aspects of the present disclosure, hybridization buffer formulations are described which, in combination with the disclosed low-binding supports, provide for improved hybridization rates, hybridization specificity (or stringency), and hybridization efficiency (or yield). As used herein, hybridization specificity is a measure of the ability of tethered adapter sequences, primer sequences, or oligonucleotide sequences in general to correctly hybridize only to completely complementary sequences, while hybridization efficiency is a measure of the percentage of total available tethered adapter sequences, primer sequences, or oligonucleotide sequences in general that are hybridized to complementary sequences.

Improved hybridization specificity and/or efficiency may be achieved through optimization of the hybridization buffer formulation used with the disclosed low-binding surfaces, and will be discussed in more detail in the examples below. Examples of hybridization buffer components that may be adjusted to achieve improved performance include, but are not limited to, buffer type, organic solvent mixtures, buffer pH, buffer viscosity, detergents and zwitterionic components, ionic strength (including adjustment of both monovalent and divalent ion concentrations), antioxidants and reducing agents, carbohydrates, BSA, polyethylene glycol, dextran sulfate, betaine, other additives, and the like.

By way of non-limiting example, suitable buffers for use in formulating a hybridization buffer may include, but are not limited to, phosphate buffered saline (PBS), succinate, citrate, histidine, acetate, Tris, TAPS, MOPS, PIPES, HEPES, MES, and the like. The choice of appropriate buffer will generally be dependent on the target pH of the hybridization buffer solution. In general, the desired pH of the buffer solution will range from about pH 4 to about pH 8.4. In some embodiments, the buffer pH may be at least 4.0, at least 4.5, at least 5.0, at least 5.5, at least 6.0, at least 6.2, at least 6.4, at least 6.6, at least 6.8, at least 7.0, at least 7.2, at least 7.4, at least 7.6, at least 7.8, at least 8.0, at least 8.2, or at least 8.4. In some embodiments, the buffer pH may be at most 8.4, at most 8.2, at most 8.0, at most 7.8, at most 7.6, at most 7.4, at most 7.2, at most 7.0, at most 6.8, at most 6.6, at most 6.4, at most 6.2, at most 6.0, at most 5.5, at most 5.0, at most 4.5, or at most 4.0. Any of the lower and upper values described in this paragraph may be combined to form a range included within the present disclosure, for example, in some instances, the desired pH may range from about 6.4 to about 7.2. Those of skill in the art will recognize that the buffer pH may have any value within this range, for example, about 7.25.

Suitable detergents for use in hybridization buffer formulation include, but are not limited to, zitterionic detergents (e.g., 1-Dodecanoyl-sn-glycero-3-phosphocholine, 3-(4-tert-Butyl-1-pyridinio)-1-propanesulfonate, 3-(N,N-Dimethylmyristylammonio)propanesulfonate, 3-(N,NDimethylmyristylammonio) propanesulfonate, ASB-C80, C7BzO, CHAPS, CHAPS hydrate, CHAPSO, DDMAB, Dimethylethylammoniumpropane sulfonate, N,N-Dimethyldodecylamine Noxide, N-Dodecyl-N,N-dimethyl-3-ammonio-1-propanesulfonate, or N-Dodecyl-N,N-dimethyl-3-ammonio-1-propanesulfonate) and anionic, cationic, and non-ionic detergents. Examples of nonionic detergents include poly(oxyethylene) ethers and related polymers (e.g. Brij®, TWEEN®, TRITON®, TRITON X-100 and IGEPAL® CA-630), bile salts, and glycosidic detergents.

The use of the disclosed low-binding supports either alone or in combination with optimized buffer formulations may yield relative hybridization rates that range from about 2× to about 20× faster than that for a conventional hybridization protocol. In some instances, the relative hybridization rate may be at least 2×, at least 3×, at least 4×, at least 5×, at least 6×, at least 7×, at least 8×, at least 9×, at least 10×, at least 12×, at least 14×, at least 16×, at least 18×, at least 20×, at least 25×, at least 30×, or at least 40× that for a conventional hybridization protocol.

In some instances, the use of the disclosed low-binding supports alone or in combination with optimized buffer formulations may yield total hybridization reaction times (i.e., the time required to reach 90%, 95%, 98%, or 99% completion of the hybridization reaction) of less than 60 minutes, 50 minutes, 40 minutes, 30 minutes, 20 minutes, 15 minutes, 10 minutes, or 5 minutes for any of these completion metrics.

In some instances, the use of the disclosed low-binding supports alone or in combination with optimized buffer formulations may yield improved hybridization specificity compared to that for a conventional hybridization protocol. In some instances, the hybridization specificity that may be achieved is better than 1 base mismatch in 10 hybridization events, 1 base mismatch in 20 hybridization events, 1 base mismatch in 30 hybridization events, 1 base mismatch in 40 hybridization events, 1 base mismatch in 50 hybridization events, 1 base mismatch in 75 hybridization events, 1 base mismatch in 100 hybridization events, 1 base mismatch in 200 hybridization events, 1 base mismatch in 300 hybridization events, 1 base mismatch in 400 hybridization events, 1 base mismatch in 500 hybridization events, 1 base mismatch in 600 hybridization events, 1 base mismatch in 700 hybridization events, 1 base mismatch in 800 hybridization events, 1 base mismatch in 900 hybridization events, 1 base mismatch in 1,000 hybridization events, 1 base mismatch in 2,000 hybridization events, 1 base mismatch in 3,000 hybridization events, 1 base mismatch in 4,000 hybridization events, 1 base mismatch in 5,000 hybridization events, 1 base mismatch in 6,000 hybridization events, 1 base mismatch in 7,000 hybridization events, 1 base mismatch in 8,000 hybridization events, 1 base mismatch in 9,000 hybridization events, or 1 base mismatch in 10,000 hybridization events.

In some instances, the use of the disclosed low-binding supports alone or in combination with optimized buffer formulations may yield improved hybridization efficiency (e.g., the fraction of available oligonucleotide primers on the support surface that are successfully hybridized with target oligonucleotide sequences) compared to that for a conventional hybridization protocol. In some instances, the hybridization efficiency that may be achieved is better than 50%, 60%, 70%, 80%, 85%, 90%, 95%, 98%, or 99% for any of the input target oligonucleotide concentrations specified below and in any of the hybridization reaction times specified above. In some instances, e.g., wherein the hybridization efficiency is less than 100%, the resulting surface density of target nucleic acid sequences hybridized to the support surface may be less than the surface density of oligonucleotide adapter or primer sequences on the surface.

In some instances, use of the disclosed low-binding supports for nucleic acid hybridization (or amplification) applications using conventional hybridization (or amplification) protocols, or optimized hybridization (or amplification) protocols may lead to a reduced requirement for the input concentration of target (or sample) nucleic acid molecules contacted with the support surface. For example, in some instances, the target (or sample) nucleic acid molecules may be contacted with the support surface at a concentration ranging from about 10 pM to about 1 µM (i.e., prior to annealing or amplification). In some instances, the target (or sample) nucleic acid molecules may be administered at a concentration of at least 10 pM, at least 20 pM, at least 30 pM, at least 40 pM, at least 50 pM, at least 100 pM, at least 200 pM, at least 300 pM, at least 400 pM, at least 500 pM, at least 600 pM, at least 700 pM, at least 800 pM, at least 900 pM, at least 1 nM, at least 10 nM, at least 20 nM, at least 30 nM, at least 40 nM, at least 50 nM, at least 60 nM, at least 70 nM, at least 80 nM, at least 90 nM, at least 100 nM, at least 200 nM, at least 300 nM, at least 400 nM, at least 500 nM, at least 600 nM, at leasy 700 nM, at least 800 nM, at least 900 nM, or at least 1 µM. In some instances, the target (or sample) nucleic acid molecules may be administered at a concentration of at most 1 µM, at most 900 nM, at most 800 nm, at most 700 nM, at most 600 nM, at most 500 nM, at most 400 nM, at most 300 nM, at most 200 nM, at most 100 nM, at most 90 nM, at most 80 nM, at most 70 nM, at most 60 nM, at most 50 nM, at most 40 nM, at most 30 nM, at most 20 nM, at most 10 nM, at most 1 nM, at most 900 pM, at most 800 pM, at most 700 pM, at most 600 pM, at most 500 pM, at most 400 pM, at most 300 pM, at most 200 pM, at most 100 pM, at most 90 pM, at most 80 pM, at most 70 pM, at most 60 pM, at most 50 pM, at most 40 pM, at most 30 pM, at most 20 pM, or at most 10 pM. Any of the lower and upper values described in this paragraph may be combined to form a range included within the present disclosure, for example, in some instances the target (or sample) nucleic acid molecules may be administered at a concentration ranging from about 90 pM to about 200 nM. Those of skill in the art will recognize that the target (or sample) nucleic acid molecules may be administered at a concentration having any value within this range, e.g., about 855 nM.

In some instances, the use of the disclosed low-binding supports alone or in combination with optimized hybridization buffer formulations may result in a surface density of hybridized target (or sample) oligonucleotide molecules (i.e., prior to performing any subsequent solid-phase or clonal amplification reaction) ranging from about from about 0.0001 target oligonucleotide molecules per $\mu m^2$ to about 1,000,000 target oligonucleotide molecules per $\mu m^2$. In some instances, the surface density of hybridized target oligonucleotide molecules may be at least 0.0001, at least 0.0005, at least 0.001, at least 0.005, at least 0.01, at least 0.05, at least 0.1, at least 0.5, at least 1, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per $\mu m^2$. In some instances, the surface density of hybridized target oligonucleotide molecules may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, at most 100, at most 90, at most 80, at most 70, at most 60, at most 50, at most 40, at most 30, at most 20, at most 10, at most 5, at most 1, at most 0.5, at most 0.1, at most 0.05, at most 0.01, at most 0.005, at most 0.001, at most 0.0005, or at most 0.0001 molecules per $\mu m^2$. Any of the lower and upper values described in this paragraph may be combined to form a range included within the present disclosure, for example, in some instances the surface density of hybridized target oligonucleotide molecules may range from about 3,000 molecules per $\mu m^2$ to about 20,000 molecules per $\mu m^2$. Those of skill in the art will recognize that the surface density of hybridized target oligonucleotide molecules may have any value within this range, e.g., about 2,700 molecules per $\mu m^2$.

Stated differently, in some instances the use of the disclosed low-binding supports alone or in combination with optimized hybridization buffer formulations may result in a surface density of hybridized target (or sample) oligonucleotide molecules (i.e., prior to performing any subsequent solid-phase or clonal amplification reaction) ranging from about 100 hybridized target oligonucleotide molecules per $mm^2$ to about $1 \times 10^7$ oligonucleotide molecules per $mm^2$ or from about 100 hybridized target oligonucleotide molecules per $mm^2$ to about $1 \times 10^{12}$ hybridized target oligonucleotide molecules per $mm^2$. In some instances, the surface density of hybridized target oligonucleotide molecules may be at least 100, at least 500, at least 1,000, at least 4,000, at least 5,000, at least 6,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ molecules per $mm^2$. In some instances, the surface density of hybridized target oligonucleotide molecules may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per $mm^2$. Any of the lower and upper values described in this paragraph may be combined to form a range included within the present disclosure, for example, in some instances the surface density of hybridized target oligonucleotide molecules may range from about 5,000 molecules per $mm^2$ to about 50,000 molecules per $mm^2$. Those of skill in the art will recognize that the surface density of hybridized target oligonucleotide molecules may have any value within this range, e.g., about 50,700 molecules per $mm^2$.

In some instances, the target (or sample) oligonucleotide molecules (or nucleic acid molecules) hybridized to the oligonucleotide adapter or primer molecules attached to the low-binding support surface may range in length from about 0.02 kilobases (kb) to about 20 kb or from about 0.1 kilobases (kb) to about 20 kb. In some instances, the target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 0.6 kb in length, at least 0.7 kb in length, at least 0.8 kb in length, at least 0.9 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, at least 20 kb in length, at least 30 kb in length, or at least 40 kb in length, or any intermediate value spanned by the range described herein, e.g., at least 0.85 kb in length.

In some instances, the target (or sample) oligonucleotide molecules (or nucleic acid molecules) may comprise single-stranded or double-stranded, multimeric nucleic acid molecules further comprising repeats of a regularly occurring monomer unit. In some instances, the single-stranded or double-stranded, multimeric nucleic acid molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, at least 30 kb in length, or at least 40 kb in length, or any intermediate value spanned by the range described herein, e.g., about 2.45 kb in length.

In some instances, the target (or sample) oligonucleotide molecules (or nucleic acid molecules) may comprise single-stranded or double-stranded multimeric nucleic acid molecules comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 17. Thus, in some instances, the surface density of hybridized target sequences in terms of the number of copies of a target sequence per unit area of the support surface may exceed the surface density of oligonucleotide primers even if the hybridization efficiency is less than 100%.

Nucleic acid surface amplification (NASA): As used herein, the phrase "nucleic acid surface amplification" (NASA) is used interchangeably with the phrase "solid-phase nucleic acid amplification" (or simply "solid-phase amplification"). In some aspects of the present disclosure, nucleic acid amplification formulations are described which, in combination with the disclosed low-binding supports, provide for improved amplification rates, amplification specificity, and amplification efficiency. As used herein, specific amplification refers to amplification of template library oligonucleotide strands that have been tethered to the solid support either covalently or non-covalently. As used herein, non-specific amplification refers to amplification of primer-dimers or other non-template nucleic acids. As used herein, amplification efficiency is a measure of the percentage of tethered oligonucleotides on the support surface that are successfully amplified during a given amplification cycle or amplification reaction. Nucleic acid amplification performed on surfaces disclosed herein may obtain amplification efficiencies of at least 50%, 60%, 70%, 80%, 90%, 95%, or greater than 95%, such as 98% or 99%.

Any of a variety of thermal cycling or isothermal nucleic acid amplification schemes may be used with the disclosed low-binding supports. Examples of nucleic acid amplification methods that may be utilized with the disclosed low-binding supports include, but are not limited to, polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, or single-stranded binding (SSB) protein-dependent amplification.

Often, improvements in amplification rate, amplification specificity, and amplification efficiency may be achieved using the disclosed low-binding supports alone or in combination with formulations of the amplification reaction components. In addition to inclusion of nucleotides, one or more polymerases, helicases, single-stranded binding proteins, etc. (or any combination thereof), the amplification reaction mixture may be adjusted in a variety of ways to achieve improved performance including, but are not limited to, choice of buffer type, buffer pH, organic solvent mixtures, buffer viscosity, detergents and zwitterionic components, ionic strength (including adjustment of both monovalent and divalent ion concentrations), antioxidants and reducing agents, carbohydrates, BSA, polyethylene glycol, dextran sulfate, betaine, other additives, and the like.

The use of the disclosed low-binding supports alone or in combination with optimized amplification reaction formulations may yield increased amplification rates compared to those obtained using conventional supports and amplification protocols. In some instances, the relative amplification rates that may be achieved may be at least 2×, at least 3×, at least 4×, at least 5×, at least 6×, at least 7×, at least 8×, at least 9×, at least 10×, at least 12×, at least 14×, at least 16×, at least 18×, or at least 20× that for use of conventional supports and amplification protocols for any of the amplification methods described above.

In some instances, the use of the disclosed low-binding supports alone or in combination with optimized buffer formulations may yield total amplification reaction times (i.e., the time required to reach 90%, 95%, 98%, or 99% completion of the amplification reaction) of less than 180 mins, 120 mins, 90 min, 60 minutes, 50 minutes, 40 minutes, 30 minutes, 20 minutes, 15 minutes, 10 minutes, 5 minutes, 3 minutes, 1 minute, 50 s, 40 s, 30 s, 20 s, or 10 s for any of these completion metrics.

Some low-binding support surfaces disclosed herein exhibit a ratio of specific binding to nonspecific binding of a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein. Some surfaces disclosed herein exhibit a ratio of specific to nonspecific fluorescence signal for a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein.

In some instances, the use of the disclosed low-binding supports alone or in combination with optimized amplification buffer formulations may enable faster amplification reaction times (i.e., the times required to reach 90%, 95%, 98%, or 99% completion of the amplification reaction) of no more than 60 minutes, 50 minutes, 40 minutes, 30 minutes, 20 minutes, or 10 minutes. Similarly, use of the disclosed low-binding supports alone or in combination with optimized buffer formulations may enable amplification reactions to be completed in some cases in no more than 2, 3, 4, 5, 6, 7, 8, 9, 10, 15, or no more than 30 cycles.

In some instances, the use of the disclosed low-binding supports alone or in combination with optimized amplification reaction formulations may yield increased specific amplification and/or decreased non-specific amplification compared to that obtained using conventional supports and amplification protocols. In some instances, the resulting ratio of specific amplification-to-non-specific amplification that may be achieved is at least 4:1 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1,000:1.

In some instances, the use of the low-binding supports alone or in combination with optimized amplification reaction formulations may yield increased amplification efficiency compared to that obtained using conventional supports and amplification protocols. In some instances, the amplification efficiency that may be achieved is better than 50%, 60%, 70% 80%, 85%, 90%, 95%, 98%, or 99% in any of the amplification reaction times specified above.

In some instances, the clonally-amplified target (or sample) oligonucleotide molecules (or nucleic acid molecules) hybridized to the oligonucleotide adapter or primer molecules attached to the low-binding support surface may range in length from about 0.02 kilobases (kb) to about 20 kb or from about 0.1 kilobases (kb) to about 20 kb. In some instances, the clonally-amplified target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., at least 0.85 kb in length.

In some instances, the clonally-amplified target (or sample) oligonucleotide molecules (or nucleic acid molecules) may comprise single-stranded or double-stranded, multimeric nucleic acid molecules further comprising repeats of a regularly occurring monomer unit. In some instances, the clonally-amplified single-stranded or double-stranded, multimeric nucleic acid molecules may be at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., about 2.45 kb in length.

In some instances, the clonally-amplified target (or sample) oligonucleotide molecules (or nucleic acid molecules) may comprise single-stranded or double-stranded multimeric nucleic acid molecules comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 12. Thus, in some instances, the surface density of clonally-amplified target sequences in terms of the number of copies of a target sequence per unit area of the support surface may exceed the surface density of oligonucleotide primers even if the hybridization and/or amplification efficiencies are less than 100%.

In some instances, the use of the disclosed low-binding supports alone or in combination with optimized amplification reaction formulations may yield increased clonal copy number compared to that obtained using conventional supports and amplification protocols. In some instances, e.g., wherein the clonally-amplified target (or sample) oligonucleotide molecules comprise concatenated, multimeric repeats of a monomeric target sequence, the clonal copy number may be substantially smaller than compared to that obtained using conventional supports and amplification protocols. Thus, in some instances, the clonal copy number may range from about 1 molecule to about 100,000 molecules (e.g., target sequence molecules) per amplified colony. In some instances, the clonal copy number may be at least 1, at least 5, at least 10, at least 50, at least 100, at least 500, at least 1,000, at least 2,000, at least 3,000, at least 4,000, at least 5,000, at least 6,000, at least 7,000, at least 8,000, at least 9,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, or at least 100,000 molecules per amplified colony. In some instances, the clonal copy number may be at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,000, at most 8,000, at most 7,000, at most 6,000, at most 5,000, at most 4,000, at most 3,000, at most 2,000, at most 1,000, at most 500, at most 100, at most 50, at most 10, at most 5, or at most 1 molecule per amplified colony. Any of the lower and upper values described in this paragraph may be combined to form a range included within the present disclosure, for example, in some instances the clonal copy number may range from about 2,000 molecules to about 9,000 molecules. Those of skill in the art will recognize that the clonal copy number may have any value within this range, e.g., about 2,220 molecules in some instances, or about 2 molecules in others.

As noted above, in some instances the amplified target (or sample) oligonucleotide molecules (or nucleic acid molecules) may comprise concatenated, multimeric repeats of a monomeric target sequence. In some instances, the amplified target (or sample) oligonucleotide molecules (or nucleic acid molecules) may comprise a plurality of molecules each of which comprises a single monomeric target sequence. Thus, the use of the disclosed low-binding supports alone or in combination with optimized amplification reaction formulations may result in a surface density of target sequence copies that ranges from about 100 target sequence copies per $mm^2$ to about $1\times10^{12}$ target sequence copies per $mm^2$. In some instances, the surface density of target sequence copies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1\times10^7$, at least $5\times10^7$, at least $1\times10^8$, at least $5\times10^8$, at least $1\times10^9$, at least $5\times10^9$, at least $1\times10^{10}$, at least $5\times10^{10}$, at least $1\times10^{11}$, at least $5\times10^{11}$, or at least $1\times10^{12}$ of clonally amplified target sequence molecules per $mm^2$. In some instances, the surface density of target sequence copies may be at most $1\times10^{12}$, at most $5\times10^{11}$, at most $1\times10^{11}$, at most $5\times10^{10}$, at most $1\times10^{10}$, at most $5\times10^9$, at most $1\times10^9$, at most $5\times10^8$, at most $1\times10^8$, at most $5\times10^7$, at most $1\times10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 target sequence copies per $mm^2$. Any of the lower and upper values described in this paragraph may be combined to form a range included within the present disclosure, for example, in some instances the surface density of target sequence copies may range from about 1,000 target sequence copies per $mm^2$ to about 65,000 target sequence copies $mm^2$. Those of skill in the art will recognize that the surface density of target sequence copies may have any value within this range, e.g., about 49,600 target sequence copies per $mm^2$.

In some instances, the use of the disclosed low-binding supports alone or in combination with optimized amplification buffer formulations may result in a surface density of clonally-amplified target (or sample) oligonucleotide molecules (or clusters) ranging from about from about 100 molecules per $mm^2$ to about $1\times10^{12}$ colonies per $mm^2$. In some instances, the surface density of clonally-amplified molecules may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1\times10^7$, at least $5\times10^7$, at least $1\times10^8$, at least $5\times10^8$, at least $1\times10^9$, at least $5\times10^9$, at least $1\times10^{10}$, at least $5\times10^{10}$, at least $1\times10^{11}$, at least $5\times10^{11}$, or at least $1\times10^{12}$ molecules per $mm^2$. In some instances, the surface density of clonally-amplified molecules may be at most $1\times10^{12}$, at most $5\times10^{11}$, at most $1\times10^{11}$, at most $5\times10^{10}$, at most $1\times10^{10}$, at most $5\times10^9$, at most $1\times10^9$, at most $5\times10^8$, at most $1\times10^8$, at most $5\times10^7$, at most $1\times10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per $mm^2$. Any of the lower and upper values described in this paragraph may be combined to form a range included within the present disclosure, for example, in some instances the surface density of clonally-amplified molecules may range from about 5,000 molecules per $mm^2$ to about 50,000 molecules per $mm^2$. Those of skill in the art will recognize that the surface density of clonally-amplified colonies may have any value within this range, e.g., about 48,800 molecules per $mm^2$.

In some instances, the use of the disclosed low-binding supports alone or in combination with optimized amplification buffer formulations may result in a surface density of clonally-amplified target (or sample) oligonucleotide molecules (or clusters) ranging from about from about 100 molecules per $mm^2$ to about $1\times10^9$ colonies per $mm^2$. In some instances, the surface density of clonally-amplified molecules may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1\times10^7$, at least $5\times10^7$, at least $1\times10^8$, at least $5\times10^8$, at least $1\times10^9$, at least molecules per $mm^2$. In some instances, the surface density of clonally-amplified molecules may be at $1\times10^9$, at most $5\times10^8$, at most $1\times10^8$, at most $5\times10^7$, at most $1\times10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per $mm^2$. Any of the lower and upper values described in this paragraph may be combined to form a range included within the present disclosure, for example, in some instances the surface density of clonally-amplified molecules may range from about 5,000 molecules per $mm^2$ to about 50,000 molecules per $mm^2$. Those of skill in the art will recognize that the surface density of clonally-amplified colonies may have any value within this range, e.g., about 48,800 molecules per $mm^2$.

In some instances, the use of the disclosed low-binding supports alone or in combination with optimized amplification buffer formulations may result in a surface density of clonally-amplified target (or sample) oligonucleotide colonies (or clusters) ranging from about from about 100 colonies per $mm^2$ to about $1 \times 10^9$ colonies per $mm^2$. In some instances, the surface density of clonally-amplified colonies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ colonies per $mm^2$. In some instances, the surface density of clonally-amplified colonies may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 colonies per $mm^2$. Any of the lower and upper values described in this paragraph may be combined to form a range included within the present disclosure, for example, in some instances the surface density of clonally-amplified colonies may range from about 5,000 colonies per $mm^2$ to about 50,000 colonies per $mm^2$. Those of skill in the art will recognize that the surface density of clonally-amplified colonies may have any value within this range, e.g., about 48,800 colonies per $mm^2$.

In some cases the use of the disclosed low-binding supports alone or in combination with optimized amplification reaction formulations may yield signal from the amplified and labeled nucleic acid populations (e.g., a fluorescence signal) that has a coefficient of variance of no greater than 50%, such as 50%, 40%, 30%, 20%, 15%, 10%, 5%, or less than 5%.

Similarly, in some cases the use of optimized amplification reaction formulations in combination with the disclosed low-binding supports yield signal from the nucleic acid populations that has a coefficient of variance of no greater than 50%, such as 50%, 40%, 30%, 20%, 10% or less than 10%.

In some cases, the support surfaces and methods as disclosed herein allow amplification at elevated extension temperatures, such as at 15 C, 20 C, 25 C, 30 C, 40 C, or greater, or for example at about 21 C or 23 C.

In some cases, the use of the support surfaces and methods as disclosed herein enable simplified amplification reactions. For example, in some cases amplification reactions are performed using no more than 1, 2, 3, 4, or 5 discrete reagents.

In some cases, the use of the support surfaces and methods as disclosed herein enable the use of simplified temperature profiles during amplification, such that reactions are executed at temperatures ranging from a low temperature of 15 C, 20 C, 25 C, 30 C, or 40 C, to a high temperature of 40 C, 45 C, 50 C, 60 C, 65 C, 70 C, 75 C, 80 C, or greater than 80 C, for example, such as a range of 20 C to 65 C.

Amplification reactions are also improved such that lower amounts of template (e.g., target or sample molecules) are sufficient to lead to discernable signals on a surface, such as 1 pM, 2 pM, 5 pM, 10 pM, 15 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, 900 pM, 1,000 pM, 2,000 pM, 3,000 pM, 4,000 pM, 5,000 pM, 6,000 pM, 7,000 pM, 8,000 pM, 9,000 pM, 10,000 pM or greater than 10,000 pM of a sample, such as 500 nM. In exemplary embodiments, inputs of about 100 pM are sufficient to generate signals for reliable signal determination.

Fluorescence imaging of support surfaces: The disclosed solid-phase nucleic acid amplification reaction formulations and low-binding supports may be used in any of a variety of nucleic acid analysis applications, e.g., nucleic acid base discrimination, nucleic acid base classification, nucleic acid base calling, nucleic acid detection applications, nucleic acid sequencing applications, and nucleic acid-based (genetic and genomic) diagnostic applications. In many of these applications, fluorescence imaging techniques may be used to monitor hybridization, amplification, and/or sequencing reactions performed on the low-binding supports.

Fluorescence imaging may be performed using any of a variety of fluorophores, fluorescence imaging techniques, and fluorescence imaging instruments known to those of skill in the art. Examples of suitable fluorescence dyes that may be used (e.g., by conjugation to nucleotides, oligonucleotides, or proteins) include, but are not limited to, fluorescein, rhodamine, coumarin, cyanine, and derivatives thereof, including the cyanine derivatives Cyanine dye-3 (Cy3), Cyanine dye-5 (Cy5), Cyanine dye-7 (Cy7), etc. Examples of fluorescence imaging techniques that may be used include, but are not limited to, wide-field fluorescence microscopy fluorescence microscopy imaging, fluorescence confocal imaging, two-photon fluorescence, and the like. Examples of fluorescence imaging instruments that may be used include, but are not limited to, fluorescence microscopes equipped with an image sensor or camera, wide-field fluorescence microscopy, confocal fluorescence microscopes, two-photon fluorescence microscopes, or custom instruments that comprise a suitable selection of light sources, lenses, mirrors, prisms, dichroic reflectors, apertures, and image sensors or cameras, etc. A non-limiting example of a fluorescence microscope equipped for acquiring images of the disclosed low-binding support surfaces and clonally-amplified colonies (or clusters) of target nucleic acid sequences hybridized thereon is the Olympus IX83 inverted fluorescence microscope equipped with) 20×, 0.75 NA, a 532 nm light source, a bandpass and dichroic mirror filter set optimized for 532 nm long-pass excitation and Cy3 fluorescence emission filter, a Semrock 532 nm dichroic reflector, and a camera (Andor sCMOS, Zyla 4.2) where the excitation light intensity is adjusted to avoid signal saturation. Often, the support surface may be immersed in a buffer (e.g., 25 mM ACES, pH 7.4 buffer) while the image is acquired.

In some instances, the performance of nucleic acid hybridization and/or amplification reactions using the disclosed reaction formulations and low-binding supports may be assessed using fluorescence imaging techniques, where the contrast-to-noise ratio (CNR) of the images provides a key metric in assessing amplification specificity and non-specific binding on the support. CNR is commonly defined as: CNR=(Signal−Background)/Noise. The background term is commonly taken to be the signal measured for the interstitial regions surrounding a particular feature (diffraction limited spot, DLS) in a specified region of interest (ROI). While signal-to-noise ratio (SNR) is often considered to be a benchmark of overall signal quality, it can be shown that improved CNR can provide a significant advantage over SNR as a benchmark for signal quality in applications that require rapid image capture (e.g., sequencing applications for which cycle times must be minimized), as shown in the example below. At high CNR the imaging time required to reach accurate discrimination (and thus accurate base-calling in the case of sequencing applications) can be drastically reduced even with moderate improvements in CNR.

In most ensemble-based sequencing approaches, the background term is typically measured as the signal associated with 'interstitial' regions. In addition to "interstitial" background ($B_{inter}$), "intrastitial" background ($B_{intra}$) exists within the region occupied by an amplified DNA colony. The combination of these two background signals dictates the achievable CNR, and subsequently directly impacts the optical instrument requirements, architecture costs, reagent costs, run-times, cost/genome, and ultimately the accuracy and data quality for cyclic array-based sequencing applications. The $B_{inter}$ background signal arises from a variety of sources; a few examples include auto-fluorescence from consumable flow cells, non-specific adsorption of detection molecules that yield spurious fluorescence signals that may obscure the signal from the ROI, the presence of non-specific DNA amplification products (e.g., those arising from primer dimers). In typical next generation sequencing (NGS) applications, this background signal in the current field-of-view (FOV) is averaged over time and subtracted. The signal arising from individual DNA colonies (i.e., (S)−$B_{inter}$ in the FOV) yields a discernable feature that can be classified. In some instances, the intrastitial background ($B_{intra}$) can contribute a confounding fluorescence signal that is not specific to the target of interest, but is present in the same ROI thus making it far more difficult to average and subtract.

As will be demonstrated in the examples below, the implementation of nucleic acid amplification on the low-binding substrates of the present disclosure may decrease the $B_{inter}$ background signal by reducing non-specific binding, may lead to improvements in specific nucleic acid amplification, and may lead to a decrease in non-specific amplification that can impact the background signal arising from both the interstitial and intrastitial regions. In some instances, the disclosed low-binding support surfaces, optionally used in combination with the disclosed hybridization and/or amplification reaction formulations, may lead to improvements in CNR by a factor of 2, 5, 10, 100, or 1000-fold over those achieved using conventional supports and hybridization, amplification, and/or sequencing protocols. Although described here in the context of using fluorescence imaging as the readout or detection mode, the same principles apply to the use of the disclosed low-binding supports and nucleic acid hybridization and amplification formulations for other detection modes as well, including both optical and non-optical detection modes.

The disclosed low-binding supports, optionally used in combination with the disclosed hybridization and/or amplification protocols, yield solid-phase reactions that exhibit: (i) negligible non-specific binding of protein and other reaction components (thus minimizing substrate background), (ii) negligible non-specific nucleic acid amplification product, and (iii) provide tunable nucleic acid amplification reactions. Although described herein primarily in the context of nucleic acid hybridization, amplification, and sequencing assays, it will be understood by those of skill in the art that the disclosed low-binding supports may be used in any of a variety of other bioassay formats including, but not limited to, sandwich immunoassays, enzyme-linked immunosorbent assays (ELISAs), etc.

Plastic surface: Examples of materials from which the substrate or support structure may be fabricated include, but are not limited to, glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), or any combination thereof. Various compositions of both glass and plastic substrates are contemplated.

Modification of a surface for the purposes disclosed herein involves making surfaces reactive against many chemical groups (—R), including amines. When prepared on an appropriate substrate, these reactive surfaces can be stored long term at room temperature for example for at least 3 months or more. Such surfaces can be further grafted with R-PEG and R-primer oligomer for on-surface amplification of nucleic acids, as described elsewhere herein. Plastic surfaces, such as cyclic olefin polymer (COP), may be modified using any of a large number of methods known in the art. For example, they can be treated with Ti: Sapphire laser ablation, UV-mediated ethylene glycol methacrylate photografting, plasma treatment, or mechanical agitation (e.g., sand blasting, or polishing, etc.) to create hydrophilic surfaces that can stay reactive for months against many chemical groups, such as amines. These groups may then allow conjugation of passivation polymers such as PEG, or biomolecules such as DNA or proteins, without loss of biochemical activity. For example, attachment of DNA primer oligomers allows DNA amplification on a passivated plastic surface while minimizing the non-specific adsorption of proteins, fluorophore molecules, or other hydrophobic molecules.

Additionally, surface modification can be combined with, e.g., laser printing or UV masking, to create patterned surfaces. This allows patterned attachment of DNA oligomers, proteins, or other moieties, providing for surface-based enzymatic activity, binding, detection, or processing. For example, DNA oligomers may be used to amplify DNA only within patterned features, or to capture amplified long DNA concatemers in a patterned fashion. In some embodiments, enzyme islands may be generated in the patterned areas that are capable of reacting with solution-based substrates. Because plastic surfaces are especially amenable to these processing modes, in some embodiments as contemplated herein, plastic surfaces may be recognized as being particularly advantageous.

Furthermore, plastic can be injection molded, embossed, or 3D printed to form any shape, including microfluidic devices, much more easily than glass substrates, and thus can be used to create surfaces for the binding and analysis of biological samples in multiple configurations, e.g., sample-to-result microfluidic chips for biomarker detection or DNA sequencing.

Specific localized DNA amplification on modified plastic surfaces can be prepared and can produce spots with an ultra-high contrast to noise ratio and very low background when probed with fluorescent labels.

Hydrophilized and amine reactive cyclic olefin polymer surface with amine-primer and amine-PEG can be prepared and it supports rolling circle amplification. When probed with fluorophore labeled primers, or when labeled dNTPs added to the hybridized primers by a polymerase, bright spots of DNA amplicons were observed that exhibited signal to noise ratios greater than 100 with backgrounds that are extremely low, indicating highly specific amplification, and ultra-low levels of protein and hydrophobic fluorophore binding which are hallmarks of the high accuracy detection systems such as fluorescence-based DNA sequencers.

Oligonucleotide primers and adapter sequences: In general, at least one layer of the one or more surface modification or polymer layers applied to the capillary or channel lumen surface may comprise functional groups for covalently or non-covalently attaching oligonucleotide adapter or primer sequences, or the at least one layer may already comprise covalently or non-covalently attached oligonucleotide adapter or primer sequences at the time that it is grafted to or deposited on the support surface. In some aspects, the capillary or the microfluidic channel comprises an oligonucleotide population directed to sequence a prokaryotic genome. In some aspects, the capillary or the microfluidic channel comprises an oligonucleotide population directed to sequence a transcriptome.

The central region of the flow cell devices or systems can include a surface having at least one oligonucleotide tethered thereto. In some embodiments, the surface can be an interior surface of a microfluidic channel or capillary tube. In some aspects, the surface is a locally planar surface. In some embodiments, the oligonucleotide is directly tethered to the surface. In some embodiments, the oligonucleotide is tethered to the surface through an intermediate molecule.

The oligonucleotide tethered to the interior surface of the central region can include segments that bind to different targets. In some instance, the oligonucleotide exhibits a segment that specifically hybridizes to a eukaryotic genomic nucleic acid segment. In some instance, the oligonucleotide exhibits a segment that specifically hybridizes to a prokaryotic genomic nucleic acid segment. In some instance, the oligonucleotide exhibits a segment that specifically hybridizes to a viral nucleic acid segment. In some instance, the oligonucleotide exhibits a segment that specifically hybridizes to a transcriptome nucleic acid segment. When the central region comprises a surface having one or more oligonucleotide tethered thereto, the interior volume of the central region can be adjusted based on the types of sequencing performed. In some embodiments, the central region comprises an interior volume suitable for sequencing a eukaryotic genome. In some embodiments, the central region comprises an interior volume suitable for sequencing a prokaryotic genome. In some embodiments, the central region comprises an interior volume suitable for sequencing a transcriptome. For example, in some embodiments, the interior volume of the central region may comprise a volume of less than 0.05 µl, between 0.05 µl and 0.1 between 0.05 µl and 0.2 between 0.05 µl and 0.5 between 0.05 µl and 0.8 between 0.05 µl and 1 between 0.05 µl and 1.2 between 0.05 µl and 1.5 between 0.1 µl and 1.5 between 0.2 µl and 1.5 between 0.5 µl and 1.5 between 0.8 µl and 1.5 between 1 µl and 1.5 between 1.2 µl and 1.5 or greater than 1.5 or a range defined by any two of the foregoing. In some embodiments, the interior volume of the central region may comprise a volume of less than 0.4 µl, between 0.5 µl and 1 between 0.5 µl and 2 between 0.5 µl and 5 between 0.5 µl and 8 between 0.5 µl and 10 between 0.5 µl and 12 µl, between 0.5 µl and 15 between 1 µl and 15 between 2 µl and 15 between 5 µl and 15 between 8 µl and 15 between 10 µl and 15 between 12 µl and 15 µl or greater than 15 µl, or a range defined by any two of the foregoing. In some embodiments, the interior volume of the central region may comprise a volume of less than 5 µl, between 5 µl and 10 between 5 µl and 20 µl between 5 µl and 500 between 5 µl and 80 between 5 µl and 100 between 5 µl and 120 between 5 µl and 150 between 10 µl and 150 between 20 µl and 150 between 50 µl and 150 between 80 µl and 150 between 100 µl and 150 between 120 µl and 150 or greater than 150 or a range defined by any two of the foregoing. In some embodiments, the interior volume of the central region may comprise a volume of less than 50 µl, between 50 µl and 100 µl, between 50 µl and 200 between 50 µl and 500 between 50 µl and 800 between 50 µl and 1000 between 50 µl and 1200 between 50 µl and 1500 between 100 µl and 1500 between 200 µl and 1500 between 500 µl and 1500 between 800 µl and 1500 between 1000 µl and 1500 between 1200 µl and 1500 or greater than 1500 or a range defined by any two of the foregoing. In some embodiments, the interior volume of the central region may comprise a volume of less than 500 µl, between 500 µl and 1000 between 500 µl and 2000 between 500 µl and 5 ml, between 500 µl and 8 ml, between 500 µl and 10 ml, between 500 µl and 12 ml, between 500 µl and 15 ml, between 1 ml and 15 ml, between 2 ml and 15 ml, between 5 ml and 15 ml, between 8 ml and 15 ml, between 10 ml and 15 ml, between 12 ml and 15 ml, or greater than 15 ml, or a range defined by any two of the foregoing. In some embodiments, the interior volume of the central region may comprise a volume of less than 5 ml, between 5 ml and 10 ml, between 5 ml and 20 ml, between 5 ml and 50 ml, between 5 ml and 80 ml, between 5 ml and 100 ml, between 5 ml and 120 ml, between 5 ml and 150 ml, between 10 ml and 150 ml, between 20 ml and 150 ml, between 50 ml and 150 ml, between 80 ml and 150 ml, between 100 ml and 150 ml, between 120 ml and 150 ml, or greater than 150 ml, or a range defined by any two of the foregoing. In some embodiments, the methods and systems described herein comprise an array or collection of flow cell devices or systems comprising multiple discrete capillaries, microfluidic channels, fluidic channels, chambers, or lumenal regions, wherein the combined interior volume is, comprises, or includes one or more of the values within a range disclosed herein.

One or more types of oligonucleotide primer may be attached or tethered to the support surface. In some instances, the one or more types of oligonucleotide adapters or primers may comprise spacer sequences, adapter sequences for hybridization to adapter-ligated template library nucleic acid sequences, forward amplification primers, reverse amplification primers, sequencing primers, and/or molecular barcoding sequences, or any combination thereof.

The tethered oligonucleotide adapter and/or primer sequences may range in length from about 10 nucleotides to about 100 nucleotides. In some instances, the tethered oligonucleotide adapter and/or primer sequences may be no more than 10, at least 10, at least 20, at least 30, at least 40, at least 50, at least 60, at least 70, at least 80, at least 90, or at least 100 nucleotides in length. In some instances, the tethered oligonucleotide adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered oligonucleotide adapter and/or primer sequences may range from about 20 nucleotides to about 80 nucleotides. Those of skill in the art will recognize that the length of the tethered oligonucleotide adapter and/or primer sequences may have any value within this range, e.g., about 24 nucleotides.

The number of coating layers and/or the material composition of each layer is chosen so as to adjust the resultant surface density of oligonucleotide primers (or other attached molecules) on the coated capillary lumen surface. In some instances, the surface density of oligonucleotide primers may range from about 1,000 primer molecules per $\mu m^2$ to about 1,000,000 primer molecules per $\mu m^2$. In some instances, the surface density of oligonucleotide primers may be at least 1,000, at least 10,000, at least 100,000, or at least 1,000,000 molecules per $\mu m^2$. In some instances, the surface density of oligonucleotide primers may be at most 1,000,000, at most 100,000, at most 10,000, or at most 1,000 molecules per $\mu m^2$. Any of the lower and upper values described in this paragraph may be combined to form a range included within the present disclosure, for example, in some instances the surface density of primers may range from about 10,000 molecules per $\mu m^2$ to about 100,000 molecules per $\mu m^2$. Those of skill in the art will recognize that the surface density of primer molecules may have any value within this range, e.g., about 455,000 molecules per $\mu m^2$. In some instances, the surface properties of the capillary or channel lumen coating, including the surface density of tethered oligonucleotide primers, may be adjusted so as to optimize, e.g., solid-phase nucleic acid hybridization specificity and efficiency, and/or solid-phase nucleic acid amplification rate, specificity, and efficiency.

Figure 2:
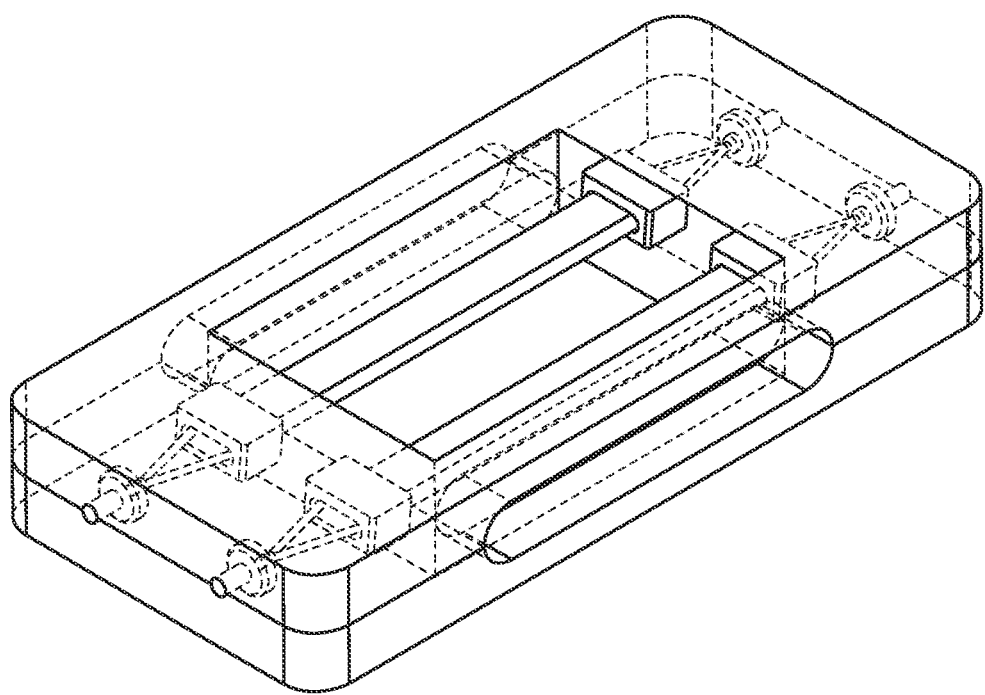
FIG. 2 illustrates one embodiment of a flow cell cartridge comprising a chassis, fluidic adapters, and two capillaries.

Capillary flow cell cartridges: Also disclosed herein are capillary flow cell cartridges that may comprise one, two, or more capillaries to create independent flow channels. FIG. 2 provides a non-limiting example of capillary flow cell cartridge that comprises two glass capillaries, fluidic adaptors (two per capillary in this example), and a cartridge chassis that mates with the capillaries and/or fluidic adapters such that the capillaries are held in a fixed orientation relative to the cartridge. In some instances, the fluidic adaptors may be integrated with the cartridge chassis. In some instances, the cartridge may comprise additional adapters that mate with the capillaries and/or capillary fluidic adapters. In some instances, the capillaries are permanently mounted in the cartridge. In some instances, the cartridge chassis is designed to allow one or more capillaries of the flow cell cartridge to be interchangeable removed and replaced. For example, in some instances, the cartridge chassis may comprise a hinged "clamshell" configuration which allows it to be opened so that one or more capillaries may be removed and replaces. In some instances, the cartridge chassis is configured to mount on, for example, the stage of a microscope system or within a cartridge holder of an instrument system.

The capillary flow cell cartridges of the present disclosure may comprise a single capillary. In some instances, the capillary flow cell cartridges of the present disclosure may comprise 2, 3, 4, 5, 6, 7, 8, 9, 10, 11, 12, 13, 14, 15, 16, 17, 18, 19, 20, or more than 20 capillaries. The one or more capillaries of the flow cell cartridge may have any of the geometries, dimensions, material compositions, and/or coatings as described above for the single capillary flow cell devices. Similarly, the fluidic adapters for the individual capillaries in the cartridge (typically two fluidic adapters per capillary) may have any of the geometries, dimensions, and material compositions as described above for the single capillary flow cell devices, except that in some instances the fluidic adapters may be integrated directly with the cartridge chassis as illustrated in FIG. 2. In some instances, the cartridge may comprise additional adapters (i.e., in addition to the fluidic adapters) that mate with the capillaries and/or fluidic adapters and help to position the capillaries within the cartridge. These adapters may be constructed using the same fabrication techniques and materials as those outlined above for the fluidic adapters.

In some embodiments, one or more devices according to the present disclosure may comprise a first surface in an orientation generally facing the interior of the flow channel, wherein said surface may further comprise a polymer coating as disclosed elsewhere herein, and wherein said surface may further comprise one or more oligonucleotides such as a capture oligonucleotide, an adapter oligonucleotide, or any other oligonucleotide as disclosed herein. In some embodiments, said devices may further comprise a second surface in an orientation generally facing the interior of the flow channel and further generally facing or parallel to the first surface, wherein said surface may further comprise a polymer coating as disclosed elsewhere herein, and wherein said surface may further comprise one or more oligonucleotides such as a capture oligonucleotide, an adapter oligonucleotide, or any other oligonucleotide as disclosed herein. In some embodiments, a device of the present disclosure may comprise a first surface in an orientation generally facing the interior of the flow channel, a second surface in an orientation generally facing the interior of the flow channel and further generally facing or parallel to the first surface, a third surface generally facing the interior of a second flow channel, and a fourth surface, generally facing the interior of the second flow channel and generally opposed to or parallel to the third surface; wherein said second and third surfaces may be located on or attached to opposite sides of a generally planar substrate which may be a reflective, transparent, or translucent substrate. In some embodiments, an imaging surface or imaging surfaces within a flowcell may be located within the center of a flowcell or within or as part of a division between two subunits or subdivisions of a flowcell, wherein said flowcell may comprise a top surface and a bottom surface, one or both of which may be transparent to such detection mode as may be utilized; and wherein a surface comprising oligonucleotides or polynucleotides and/or one or more polymer coatings, may be placed or interposed within the lumen of the flowcell. In some embodiments, the top and/or bottom surfaces do not include attached oligonucleotides or polynucleotides. In some embodiments, said top and/or bottom surfaces do comprise attached oligonucleotides and/or polynucleotides. In some embodiments, either said top or said bottom surface may comprise attached oligonucleotides and/or polynucleotides. A surface or surfaces placed or interposed within the lumen of a flowcell may be located on or attached one side, an opposite side, or both sides of a generally planar substrate which may be a reflective, transparent, or translucent substrate. In some embodiments, an optical apparatus as provided elsewhere herein or as otherwise known in the art is utilized to provide images of a first surface, a second surface, a third surface, a fourth surface, a surface interposed within the lumen of a flowcell, or any other surface provided herein which may contain one or more oligonucleotides or polynucleotides attached thereto.

Microfluidic chip flow cell cartridges: Also disclosed herein are microfluidic channel flow cell cartridges that may a plurality of independent flow channels. A non-limiting example of microfluidic chip flow cell cartridge that comprises a chip having two or more parallel glass channels formed on the chip, fluidic adaptors coupled to the chip, and a cartridge chassis that mates with the chip and/or fluidic adapters such that the chip is posited in a fixed orientation relative to the cartridge. In some instances, the fluidic adaptors may be integrated with the cartridge chassis. In some instances, the cartridge may comprise additional adapters that mate with the chip and/or fluidic adapters. In some instances, the chip is permanently mounted in the cartridge. In some instances, the cartridge chassis is designed to allow one or more chips of the flow cell cartridge to be interchangeable removed and replaced. For example, in some instances, the cartridge chassis may comprise a hinged "clamshell" configuration which allows it to be opened so that one or more capillaries may be removed and replaces. In some instances, the cartridge chassis is configured to mount on, for example, the stage of a microscope system or within a cartridge holder of an instrument system. Even through only one chip is described in the non-limiting example, it is understood that more than one chip can be used in the microfluidic channel flow cell cartridge.

The flow cell cartridges of the present disclosure may comprise a single microfluidic chip or a plurality of microfluidic chips. In some instances, the flow cell cartridges of the present disclosure may comprise 2, 3, 4, 5, 6, 7, 8, 9, 10, 11, 12, 13, 14, 15, 16, 17, 18, 19, 20, or more than 20 microfluidic chips. In some instances, the microfluidic chip can have one channel. In some instances, the microfluidic chip can have 2, 3, 4, 5, 6, 7, 8, 9, 10, 11, 12, 13, 14, 15, 16, 17, 18, 19, 20, or more than 20 channels. The one or more chips of the flow cell cartridge may have any of the geometries, dimensions, material compositions, and/or coatings as described above for the single microfluidic chip flow cell devices. Similarly, the fluidic adapters for the individual chip in the cartridge (typically two fluidic adapters per capillary) may have any of the geometries, dimensions, and material compositions as described above for the single microfluidic chip flow cell devices, except that in some instances the fluidic adapters may be integrated directly with the cartridge chassis. In some instances, the cartridge may comprise additional adapters (i.e., in addition to the fluidic adapters) that mate with the chip and/or fluidic adapters and help to position the chip within the cartridge. These adapters may be constructed using the same fabrication techniques and materials as those outlined above for the fluidic adapters.

The cartridge chassis (or "housing") may be fabricated from metal and/or polymer materials such as aluminum, anodized aluminum, polycarbonate (PC), acrylic (PMMA), or Ultem (PEI), while ohter materials are also consistent with the disclosure. A housing may be fabricated using CNC machining and/or molding techniques, and designed so that one, two, or more than two capillaries are constrained by the chassis in a fixed orientation to create independent flow channels. The capillaries may be mounted in the chassis using, e.g., a compression fit design, or by mating with compressible adapters made of silicone or a fluoroelastomer. In some instance, two or more components of the cartridge chassis (e.g., an upper half and a lower half) are assembled using, e.g., screws, clips, clamps, or other fasteners so that the two halves are separable. In some instances, two or more components of the cartridge chassis are assembled using, e.g., adhesives, solvent bonding, or laser welding so that the two or more components are permanently attached.

Some flow cell cartridges of the present disclosure further comprise additional components that are integrated with the cartridge to provide enhanced performance for specific applications. Examples of additional components that may be integrated into the cartridge include, but are not limited to, fluid flow control components (e.g., miniature valves, miniature pumps, mixing manifolds, etc.), temperature control components (e.g., resistive heating elements, metal plates that serve as heat sources or sinks, piezoelectric (Peltier) devices for heating or cooling, temperature sensors), or optical components (e.g., optical lenses, windows, filters, mirrors, prisms, fiber optics, and/or light-emitting diodes (LEDs) or other miniature light sources that may collectively be used to facilitate spectroscopic measurements and/or imaging of one or more capillary flow channels).

Systems and system components: The flow cell devices and flow cell cartridges disclosed herein may be used as components of systems designed for a variety of chemical analysis, biochemical analysis, nucleic acid analysis, cell analysis, or tissue analysis application. In general, such systems may comprise one or more fluid flow control modules, temperature control modules, spectroscopic measurement and/or imaging modules, and processors or computers, as well as one or more of the single capillary flow cell devices and capillary flow cell cartridges or the microfluidic chip flow cell devices and flow cell cartridges described herein.

The systems disclosed herein may comprise 1, 2, 3, 4, 5, 6, 7, 8, 9, 10, or more than 10 single capillary flow cell devices or capillary flow cell cartridges. In some instances the single capillary flow cell devices or capillary flow cell cartridges may be removable, exchangeable components of the disclosed systems. In some instances, the single capillary flow cell devices or capillary flow cell cartridges may be disposable or consumable components of the disclosed systems. The systems disclosed herein may comprise 1, 2, 3, 4, 5, 6, 7, 8, 9, 10, or more than 10 single microfluidic channel flow cell devices or microfluidic channel flow cell cartridges. In some instances the single microfluidic channel flow cell devices or microfluidic channel flow cell cartridges may be removable, exchangeable components of the disclosed systems. In some instances, the flow cell devices or flow cell cartridges may be disposable or consumable components of the disclosed systems.

Figure 3:
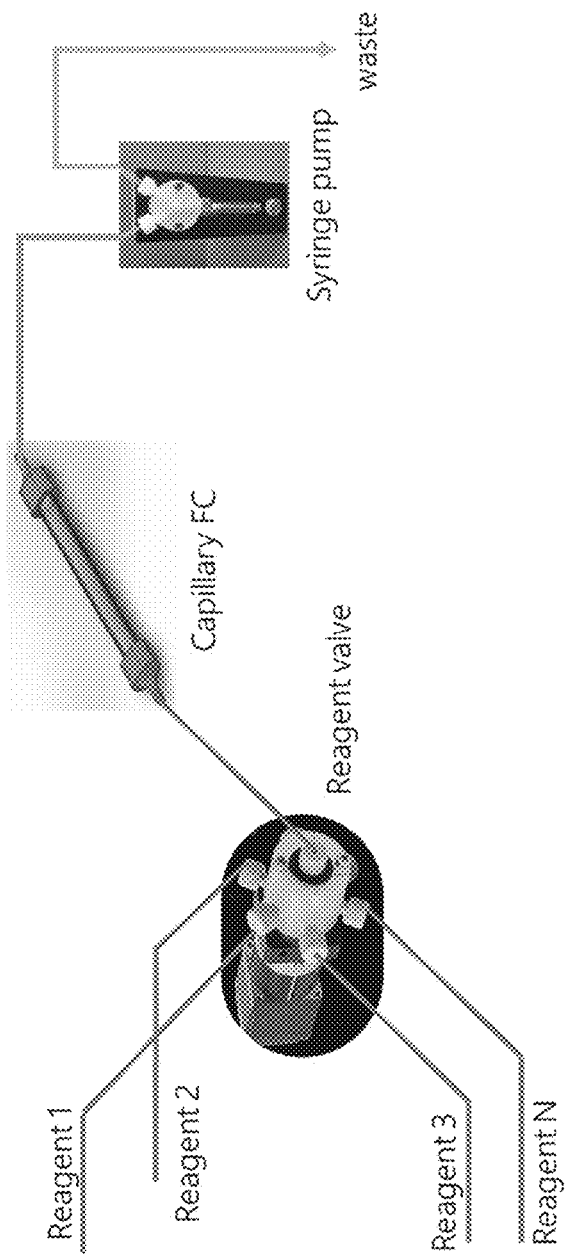
FIG. 3 illustrates one embodiment of a system comprising a single capillary flow cell connected to various fluid flow control components, where the single capillary is compatible with mounting on a microscope stage or in a custom imaging instrument for use in various imaging applications.

FIG. 3 illustrates one embodiment of a simple system comprising a single capillary flow cell connected to various fluid flow control components, where the single capillary is optically accessible and compatible with mounting on a microscope stage or in a custom imaging instrument for use in various imaging applications. A plurality of reagent reservoirs are fluidically-coupled with the inlet end of the single capillary flow cell device, where the reagent flowing through the capillary at any given point in time is controlled by means of a programmable rotary valve that allows the user to control the timing and duration of reagent flow. In this non-limiting example, fluid flow is controlled by means of a programmable syringe pump that provides precise control and timing of volumetric fluid flow and fluid flow velocity.

Figure 4:
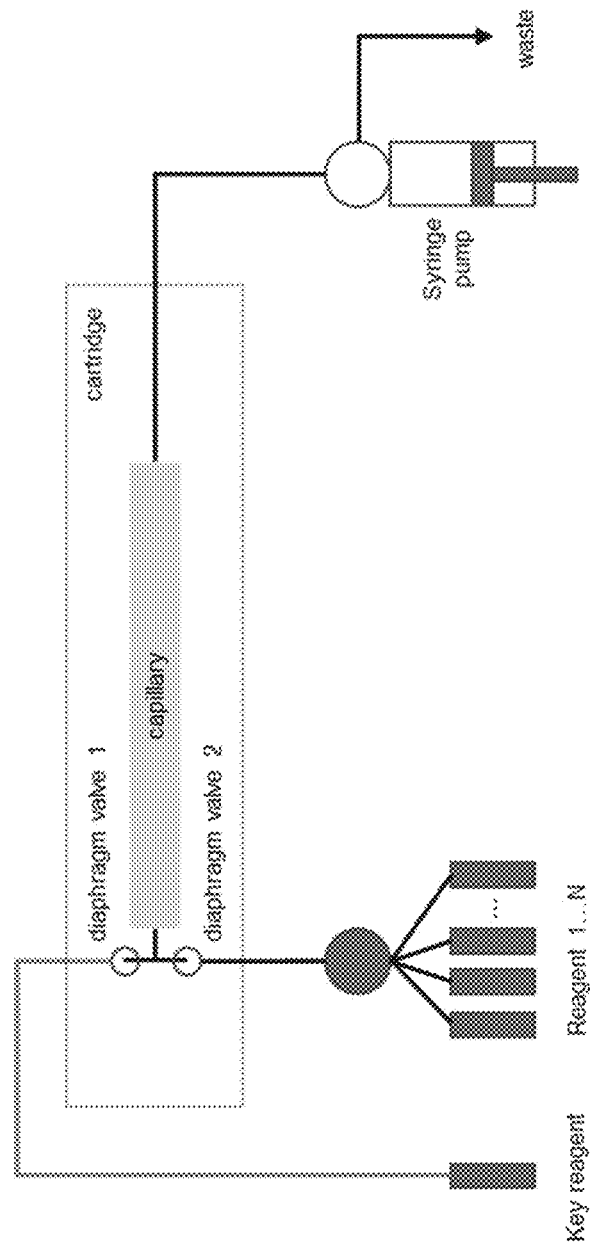
FIG. 4 illustrates one embodiment of a system that comprises a capillary flow cell cartridge having integrated diaphragm valves to minimize dead volume and conserve certain key reagents.

FIG. 4 illustrates one embodiment of a system that comprises a capillary flow cell cartridge having integrated diaphragm valves to minimize dead volume and conserve certain key reagents. The integration of miniature diaphragm valves into the cartridge allows the valve to be positioned in close proximity to the inlet of the capillary, thereby minimizing dead volume within the device and reducing the consumption of costly reagents. The integration of valves and other fluid control components within the capillary flow cell cartridge also allows greater fluid flow control functionality to be incorporated into the cartridge design.

Figure 5:
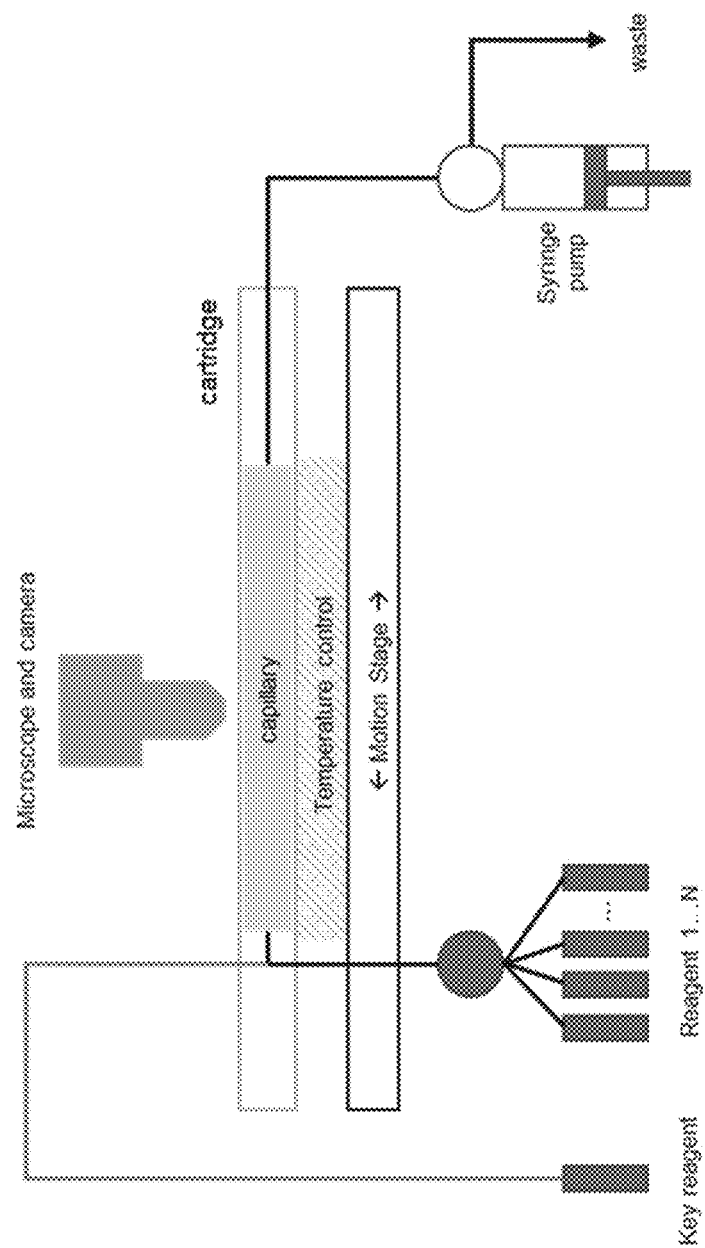
FIG. 5 illustrates one embodiment of a system that comprises a capillary flow cell, a microscope setup, and a temperature control mechanism.

FIG. 5 shows an example of a capillary flow cell cartridge-based fluidics system used in combination with a microscope setup, where the cartridge incorporates or mates with a temperature control component such as a metal plate that makes contact with the capillaries within the cartridge and serves as a heat source/sink. The microscope setup consists of an illumination system (e.g., including a laser, LED, or halogen lamp, etc., as a light source), an objective lens, an imaging system (e.g., a CMOS or CCD camera), and a translation stage to move the cartridge relative to the optical system, which allows, e.g., fluorescence and/or bright field images to be acquired for different regions of the capillary flow cells as the stage is moved.

Figure 6:
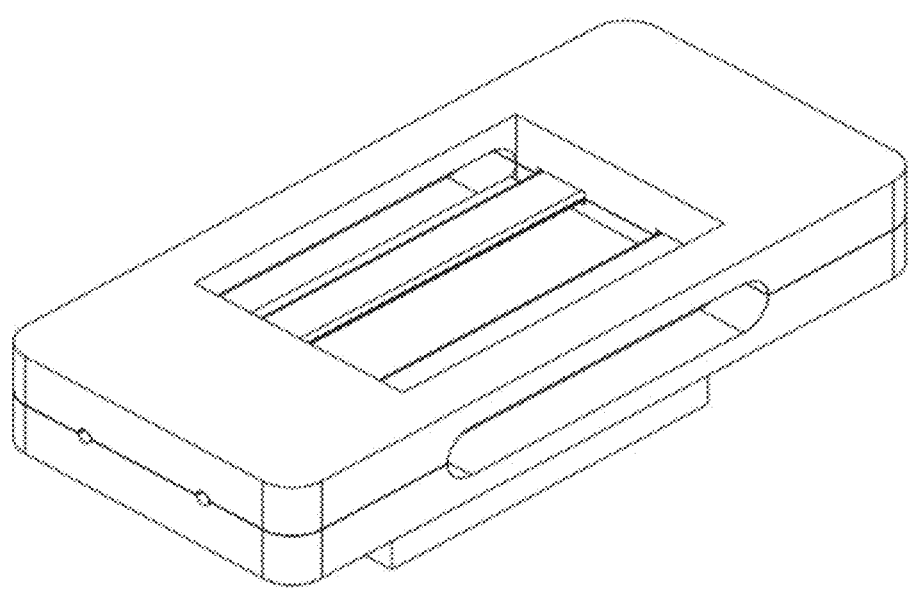
FIG. 6 illustrates one non-limiting example for temperature control of the capillary flow cells through the use of a metal plate that is placed in contact with the flow cell cartridge.

FIG. 6 illustrates one non-limiting example for temperature control of the flow cells (e.g., capillary or microfluidic channel flow cells) through the use of a metal plate that is placed in contact with the flow cell cartridge. In some instances, the metal plate may be integrated with the cartridge chassis. In some instances, the metal plate may be temperature controlled using a Peltier or resistive heater.

Figure 7:
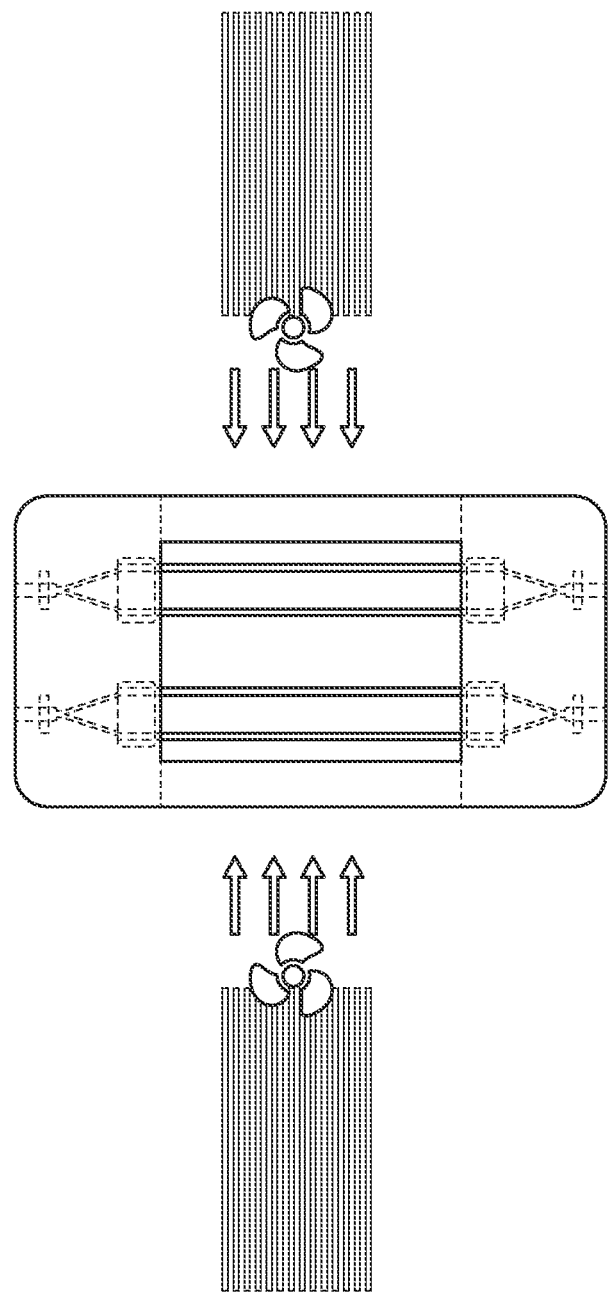
FIG. 7 illustrates one non-limiting approach for temperature control of the capillary flow cells that comprises a non-contact thermal control mechanism.

FIG. 7 illustrates one non-limiting approach for temperature control of the flow cells (e.g., capillary or microfluidic channel flow cells) that comprises a non-contact thermal control mechanism. In this approach, a stream of temperature-controlled air is directed through the flow cell cartridge (e.g., towards a single capillary flow cell device or a microfluidic channel flow cell device) using an air temperature control system. The air temperature control system comprises a heat exchanger, e.g., a resistive heater coil, fins attached to a Peltier device, etc., that is capable of heating and/or cooling the air and holding it at a constant, user-specified temperature. The air temperature control system also comprises an air delivery device, such as a fan, that directs the stream of heated or cooled air to the capillary flow cell cartridge. In some instances, the air temperature control system may be set to a constant temperature $T_1$ so that the air stream, and consequently the flow cell or cartridge (e.g., capillary flow cell or microfluidic channel flow cell) is kept at a constant temperature $T_2$, which in some cases may differ from the set temperature $T_1$ depending on the environment temperature, air flow rate, etc. In some instances, two or more such air temperature control systems may be installed around the capillary flow cell device or flow cell cartridge so that the capillary or cartridge may be rapidly cycled between several different temperatures by controlling which one of the air temperature control systems is active at a given time. In another approach, the temperature setting of the air temperature control system may be varied so the temperature of the capillary flow cell or cartridge may be changed accordingly.

Fluid flow control module: In general, the disclosed instrument systems will provide fluid flow control capability for delivering samples or reagents to the one or more flow cell devices or flow cell cartridges (e.g., single capillary flow cell device or microfluidic channel flow cell device) connected to the system. Reagents and buffers may be stored in bottles, reagent and buffer cartridges, or other suitable containers that are connected to the flow cell inlets by means of tubing and valve manifolds. The disclosed systems may also include processed sample and waste reservoirs in the form of bottles, cartridges, or other suitable containers for collecting fluids downstream of the capillary flow cell devices or capillary flow cell cartridges. In some embodiments, the fluid flow control (or "fluidics") module may provide programmable switching of flow between different sources, e.g. sample or reagent reservoirs or bottles located in the instrument, and the central region (e.g., capillary or microfluidic channel) inlet(s). In some embodiments, the fluid flow control module may provide programmable switching of flow between the central region (e.g., capillary or microfluidic channel) outlet(s) and different collection points, e.g., processed sample reservoirs, waste reservoirs, etc., connected to the system. In some instances, samples, reagents, and/or buffers may be stored within reservoirs that are integrated into the flow cell cartridge itself. In some instances, processed samples, spent reagents, and/or used buffers may be stored within reservoirs that are integrated into the flow cell cartridge itself.

Control of fluid flow through the disclosed systems will typically be performed through the use of pumps (or other fluid actuation mechanisms) and valves (e.g., programmable pumps and valves). Examples of suitable pumps include, but are not limited to, syringe pumps, programmable syringe pumps, peristaltic pumps, diaphragm pumps, and the like. Examples of suitable valves include, but are not limited to, check valves, electromechanical two-way or three-way valves, pneumatic two-way and three-way valves, and the like. In some embodiments, fluid flow through the system may be controlled by means of applying positive pneumatic pressure to one or more inlets of the reagent and buffer containers, or to inlets incorporated into flow cell cartridge(s) (e.g., capillary or microfluidic channel flow cell cartridges). In some embodiments, fluid flow through the system may be controlled by means of drawing a vacuum at one or more outlets of waste reservoir(s), or at one or more outlets incorporated into flow cell cartridge(s) (e.g., capillary or microfluidic channel flow cell cartridges).

In some instances, different modes of fluid flow control are utilized at different points in an assay or analysis procedure, e.g. forward flow (relative to the inlet and outlet for a given capillary flow cell device), reverse flow, oscillating or pulsatile flow, or combinations thereof. In some applications, oscillating or pulsatile flow may be applied, for example, during assay wash/rinse steps to facilitate complete and efficient exchange of fluids within the one or more flow cell devices or flow cell cartridges (e.g., single capillary flow cell devices or cartridges and microfluidic chip flow cell devices or cartridges).

Similarly, in some cases different fluid flow rates may be utilized at different points in the assay or analysis process workflow, for example, in some instances, the volumetric flow rate may vary from −100 ml/sec to +100 ml/sec. In some embodiment, the absolute value of the volumetric flow rate may be at least 0.001 ml/sec, at least 0.01 ml/sec, at least 0.1 ml/sec, at least 1 ml/sec, at least 10 ml/sec, or at least 100 ml/sec. In some embodiments, the absolute value of the volumetric flow rate may be at most 100 ml/sec, at most 10 ml/sec, at most 1 ml/sec, at most 0.1 ml/sec, at most 0.01 ml/sec, or at most 0.001 ml/sec. The volumetric flow rate at a given point in time may have any value within this range, e.g. a forward flow rate of 2.5 ml/sec, a reverse flow rate of −0.05 ml/sec, or a value of 0 ml/sec (i.e., stopped flow).

Temperature control module: As noted above, in some instances the disclosed systems will include temperature control functionality for the purpose of facilitating the accuracy and reproducibility of assay or analysis results. Examples of temperature control components that may be incorporated into the instrument system (or capillary flow cell cartridge) design include, but are not limited to, resistive heating elements, infrared light sources, Peltier heating or cooling devices, heat sinks, thermistors, thermocouples, and the like. In some instances, the temperature control module (or "temperature controller") may provide for a programmable temperature change at a specified, adjustable time prior to performing specific assay or analysis steps. In some instances, the temperature controller may provide for programmable changes in temperature over specified time intervals. In some embodiments, the temperature controller may further provide for cycling of temperatures between two or more set temperatures with specified frequency and ramp rates so that thermal cycling for amplification reactions may be performed.

Spectroscopy or imaging modules: As indicated above, in some instances the disclosed systems will include optical imaging or other spectroscopic measurement capabilities. For example, any of a variety of imaging modes known to those of skill in the art may be implemented including, but not limited to, bright-field, dark-field, fluorescence, luminescence, or phosphorescence imaging. In some embodiments, the central region comprises a window that allows at least a part of the central region to be illuminated and imaged. In some embodiments, the capillary tube comprises a window that allows at least a part of the capillary tube to be illuminated and imaged. In some embodiments, the microfluidic chip comprises a window that allows at least a part of the chip channel to be illuminated and imaged.

In some embodiments, single wavelength excitation and emission fluorescence imaging may be performed. In some embodiments, dual wavelength excitation and emission (or multi-wavelength excitation or emission) fluorescence imaging may be performed. In some instances, the imaging module is configured to acquire video images. The choice of imaging mode may impact the design of the flow cells devices or flow cell cartridges in that all or a portion of the capillaries or cartridge will necessarily need to be optically transparent over the spectral range of interest. In some instances, a plurality of capillaries within a capillary flow cell cartridge may be imaged in their entirety within a single image. In some embodiments, only a single capillary or a subset of capillaries within a capillary flow cell cartridge, or portions thereof, may be imaged within a single image. In some embodiments, a series of images may be "tiled" to create a single high resolution image of one, two, several, or the entire plurality of capillaries within a cartridge. In some instances, a plurality of channels within a microfluidic chip may be imaged in their entirety within a single image. In some embodiments, only a single channel or a subset of channels within a microfluidic chip, or portions thereof, may be imaged within a single image. In some embodiments, a series of images may be "tiled" to create a single high resolution image of one, two, several, or the entire plurality of capillaries or microfluidic channels within a cartridge.

A spectroscopy or imaging module may comprise, e.g., a microscope equipped with a CMOS of CCD camera. In some instances, the spectroscopy or imaging module may comprise, e.g., a custom instrument configured to perform a specific spectroscopic or imaging technique of interest. In general, the hardware associated with the imaging module may include light sources, detectors, and other optical components, as well as processors or computers.

Light sources: Any of a variety of light sources may be used to provide the imaging or excitation light, including but not limited to, tungsten lamps, tungsten-halogen lamps, arc lamps, lasers, light emitting diodes (LEDs), or laser diodes. In some instances, a combination of one or more light sources, and additional optical components, e.g. lenses, filters, apertures, diaphragms, mirrors, and the like, may be configured as an illumination system (or sub-system).

Detectors: Any of a variety of image sensors may be used for imaging purposes, including but not limited to, photodiode arrays, charge-coupled device (CCD) cameras, or complementary metal-oxide-semiconductor (CMOS) image sensors. As used herein, "imaging sensors" may be one-dimensional (linear) or two-dimensional array sensors. In many instances, a combination of one or more image sensors, and additional optical components, e.g. lenses, filters, apertures, diaphragms, mirrors, and the like, may be configured as an imaging system (or sub-system). In some instances, e.g., where spectroscopic measurements are performed by the system rather than imaging, suitable detectors may include, but are not limited to, photodiodes, avalanche photodiodes, and photomultipliers.

Other optical components: The hardware components of the spectroscopic measurement or imaging module may also include a variety of optical components for steering, shaping, filtering, or focusing light beams through the system. Examples of suitable optical components include, but are not limited to, lenses, mirrors, prisms, apertures, diffraction gratings, colored glass filters, long-pass filters, short-pass filters, bandpass filters, narrowband interference filters, broadband interference filters, dichroic reflectors, optical fibers, optical waveguides, and the like. In some instances, the spectroscopic measurement or imaging module may further comprise one or more translation stages or other motion control mechanisms for the purpose of moving capillary flow cell devices and cartridges relative to the illumination and/or detection/imaging sub-systems, or vice versa.

Total internal reflection: In some instances, the optical module or sub-system may be designed to use all or a portion of an optically transparent wall of the capillaries or microfluidic channels in flow cell devices and cartridges as a waveguide for delivering excitation light to the capillary or channel lumen(s) via total internal reflection. When incident excitation light strikes the surface of the capillary or channel lumen at an angle with respect to a normal to the surface that is larger than the critical angle (determined by the relative refractive indices of the capillary or channel wall material and the aqueous buffer within the capillary or channel), total internal reflection occurs at the surface and the light propagates through the capillary or channel wall along the length of the capillary or channel Total internal reflection generates an evanescent wave at the lumen surface which penetrates the lumen interior for extremely short distances, and which may be used to selectively excite fluorophores at the surface, e.g., labeled nucleotides that have been incorporated by a polymerase into a growing oligonucleotide through a solid-phase primer extension reaction.

Imaging processing software: In some instances, the system may further comprise a computer (or processor) and computer-readable medium that includes code for providing image processing and analysis capability. Examples of image processing and analysis capability that may be provided by the software include, but are not limited to, manual, semi-automated, or fully-automated image exposure adjustment (e.g. white balance, contrast adjustment, signal-averaging and other noise reduction capability, etc.), automated edge detection and object identification (e.g., for identifying clonally-amplified clusters of fluorescently-labeled oligonucleotides on the lumen surface of capillary flow cell devices), automated statistical analysis (e.g., for determining the number of clonally-amplified clusters of oligonucleotides identified per unit area of the capillary lumen surface, or for automated nucleotide base-calling in nucleic acid sequencing applications), and manual measurement capabilities (e.g. for measuring distances between clusters or other objects, etc.). Optionally, instrument control and image processing/analysis software may be written as separate software modules. In some embodiments, instrument control and image processing/analysis software may be incorporated into an integrated package.

System control software: In some instances, the system may comprise a computer (or processor) and a computer-readable medium that includes code for providing a user interface as well as manual, semi-automated, or fully-automated control of all system functions, e.g., control of the fluidics module, the temperature control module, and/or the spectroscopy or imaging module, as well as other data analysis and display options. The system computer or processor may be an integrated component of the system (e.g. a microprocessor or mother board embedded within the instrument) or may be a stand-alone module, for example, a main frame computer, a personal computer, or a laptop computer. Examples of fluid control functions provided by the system control software include, but are not limited to, volumetric fluid flow rates, fluid flow velocities, the timing and duration for sample and reagent addition, buffer addition, and rinse steps. Examples of temperature control functions provided by the system control software include, but are not limited to, specifying temperature set point(s) and control of the timing, duration, and ramp rates for temperature changes. Examples of spectroscopic measurement or imaging control functions provided by the system control software include, but are not limited to, autofocus capability, control of illumination or excitation light exposure times and intensities, control of image acquisition rate, exposure time, and data storage options.

Processors and computers: In some instances, the disclosed systems may comprise one or more processors or computers. The processor may be a hardware processor such as a central processing unit (CPU), a graphic processing unit (GPU), a general-purpose processing unit, or a computing platform. The processor may be comprised of any of a variety of suitable integrated circuits, microprocessors, logic devices, field-programmable gate arrays (FPGAs) and the like. In some instances, the processor may be a single core or multi core processor, or a plurality of processors may be configured for parallel processing. Although the disclosure is described with reference to a processor, other types of integrated circuits and logic devices are also applicable. The processor may have any suitable data operation capability. For example, the processor may perform 512 bit, 256 bit, 128 bit, 64 bit, 32 bit, or 16 bit data operations.

The processor or CPU can execute a sequence of machine-readable instructions, which can be embodied in a program or software. The instructions may be stored in a memory location. The instructions can be directed to the CPU, which can subsequently program or otherwise configure the CPU to implement, e.g., the system control methods of the present disclosure. Examples of operations performed by the CPU can include fetch, decode, execute, and write back.

Some processors are a processing unit of a computer system. The computer system may enable cloud-based data storage and/or computing. In some instances, the computer system may be operatively coupled to a computer network ("network") with the aid of a communication interface. The network may be the internet, an intranet and/or extranet, an intranet and/or extranet that is in communication with the internet, or a local area network (LAN). The network in some cases is a telecommunication and/or data network. The network may include one or more computer servers, which may enable distributed computing, such as cloud-based computing.

The computer system may also include computer memory or memory locations (e.g., random-access memory, read-only memory, flash memory), electronic storage units (e.g., hard disk), communication interfaces (e.g., network adapters) for communicating with one or more other systems, and peripheral devices, such as cache, other memory units, data storage units and/or electronic display adapters. In some instances, the communication interface may allow the computer to be in communication with one or more additional devices. The computer may be able to receive input data from the coupled devices for analysis. Memory units, storage units, communication interfaces, and peripheral devices may be in communication with the processor or CPU through a communication bus (solid lines), such as may be incorporated into a motherboard. A memory or storage unit may be a data storage unit (or data repository) for storing data. The memory or storage units may store files, such as drivers, libraries and saved programs. The memory or storage units may store user data, e.g., user preferences and user programs.

The system control, image processing, and/or data analysis methods as described herein can be implemented by way of machine-executable code stored in an electronic storage location of the computer system, such as, for example, in the memory or electronic storage unit. The machine-executable or machine-readable code can be provided in the form of software. During use, the code can be executed by the processor. In some cases, the code can be retrieved from the storage unit and stored in memory for ready access by the processor. In some situations, the electronic storage unit can be precluded, and machine-executable instructions are stored in memory.

In some instances, the code may be pre-compiled and configured for use with a machine having a processer adapted to execute the code. In some instances, the code may be compiled during runtime. The code can be supplied in a programming language that can be selected to enable the code to execute in a pre-compiled or as-compiled fashion.

Some aspects of the systems and methods provided herein can be embodied in software. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

In some instances, the system control, image processing, and/or data analysis methods of the present disclosure may be implemented by way of one or more algorithms. An algorithm may be implemented by way of software upon execution by the central processing unit.

Nucleic acid sequencing applications: Nucleic acid sequencing provides one non-limiting example of an application for the disclosed flow cell devices and cartridges (e.g., capillary flow cell or microfluidic chip flow cell devices and cartridges). Many "second generation" and "third generation" sequencing technologies utilize a massively parallel, cyclic array approach to sequencing-by-synthesis (SBS), in which accurate decoding of a single-stranded template oligonucleotide sequence tethered to a solid support relies on successfully classifying signals that arise from the stepwise addition of A, G, C, and T nucleotides by a polymerase to a complementary oligonucleotide strand. These methods typically require the oligonucleotide template to be modified with a known adapter sequence of fixed length, affixed to a solid support (e.g., the lumen surface(s) of the disclosed capillary or microfluidic chip flow cell devices and cartridges) in a random or patterned array by hybridization to surface-tethered probes of known sequence that is complementary to that of the adapter sequence, and then probed through a cyclic series of single base addition primer extension reactions that use, e.g., fluorescently-labeled nucleotides to identify the sequence of bases in the template oligonucleotides. These processes thus require the use of miniaturized fluidics systems that offer precise, reproducible control of the timing of reagent introduction to the flow cell in which the sequencing reactions are performed, and small volumes to minimize the consumption of costly reagents.

Existing commercially-available NGS flow cells are constructed from layers of glass that have been etched, lapped, and/or processed by other methods to meet the tight dimensional tolerances required for imaging, cooling, and/or other requirements. When flow cells are used as consumables, the costly manufacturing processes required for their fabrication result in costs per sequencing run that are too high to make sequencing routinely accessible to scientists and medical professionals in the research and clinical spaces.

This disclosure provides a low-cost flow cell architecture that includes low cost glass or polymer capillaries or microfluidic channels, fluidics adapters, and cartridge chassis. Utilizing glass or polymer capillaries that are extruded in their final cross-sectional geometry eliminates the need for multiple high-precision and costly glass manufacturing processes. Robustly constraining the orientation of the capillaries or channels and providing convenient fluidic connections using molded plastic and/or elastomeric components further reduces cost. Laser bonding the components of the polymer cartridge chassis provides a fast and efficient means of sealing the capillary or the microfluidic channels and structurally-stabilizing the capillaries or channels and flow cell cartridge without requiring the use of fasteners or adhesives.

Applications of flow cell devices and systems: The flow cell devices and systems described herein can be used in a variety of applications such as sequencing analysis to improve the efficient use of the costly reagents. For examples, a method of sequencing a nucleic acid sample and a second nucleic acid sample can include delivering a plurality of oligonucleotides to an interior surface of an at least partially transparent chamber; delivering a first nucleic acid sample to the interior surface; delivering a plurality of nonspecific reagents through a first channel to the interior surface; delivering a specific reagent through a second channel to the interior surface, wherein the second channel has a lower volume than the first channel; visualizing a sequencing reaction on the interior surface of the at least partially transparent chamber; and replacing the at least partially transparent chamber prior to a second sequencing reaction. In some aspects, flowing an air current past an exterior surface of the at least partially transparent surface. In some aspects, the described method can include selecting the plurality of oligonucleotides to sequence a eukaryotic genome. In some aspects, the described method can include selecting a prefabricated tube as the at least partially transparent chamber. In some aspects, the described method can include selecting the plurality of oligonucleotides to sequence a prokaryotic genome. In some aspects, the described method can include selecting the plurality of oligonucleotides to sequence a transcriptome. In some aspects, the described method can include selecting a capillary tube as the at least partially transparent chamber. In some aspects, the described method can include selecting a microfluidic chip as the at least partially transparent chamber.

The described devices and systems can also be used in a method of reducing a reagent used in a sequencing reaction, comprising providing a first reagent in a first reservoir; providing a second reagent in a first second reservoir, wherein each of the first reservoir and the second reservoir are fluidicaly coupled to a central region, and wherein the central region comprises a surface for the sequencing reaction; and sequentially introducing the first reagent and the second reagent into a central region of the flow cell device, wherein the volume of the first reagent flowing from the first reservoir to the inlet of the central region is less than the volume of the second reagent flowing from the second reservoir to the central region.

An additional use of the described devices and systems is a method of increasing the efficient use of a regent in a sequencing reaction, comprising: providing a first reagent in a first reservoir; providing a second reagent in a first second reservoir, wherein each of the first reservoir and the second reservoir are fluidicaly coupled to a central region, and wherein the central region comprises a surface for the sequencing reaction; and maintaining the volume of the first reagent flowing from the first reservoir to the inlet of the central region to be less than the volume of the second reagent flowing from the second reservoir to the central region.

In general, the first reagent is more expensive than the second agent. In some aspects, the first reagent is selected from the group consisting of a polymerase, a nucleotide, and a nucleotide analog.

Method of fabricating the microfluidic chip: The microfluidic chip can be manufactured by a combination of microfabrication process. The method of manufacturing the microfluidic chip described herein includes providing a surface; and forming at least one channel on the surface. The method of manufacturing can also include providing a first substrate which has at least a first planar surface, wherein the first surface has a plurality of channels; providing a second substrate having at least a second planar surface; and binding the first planar surface of the first substrate to the second planar surface of the second substrate. In some instances, the channels on the first surface have an open top side and closed bottom side, and the second surface is bond to the first surface through the bottom side of the channels and therefore leaving the open top side of the channels unaffected. In some instances, the method described herein further includes providing a third substrate having a third planar surface, and bonding the third surface to the first surface through the open top side of the channels. The bonding conditions can include, e.g., heating the substrates, or applying an adhesive to one of the planar surfaces of the first or second substrate.

Typically, because the devices are microfabricated, substrate materials will be selected based upon their compatibility with known microfabrication techniques, e.g., photolithography, wet chemical etching, laser ablation, laser irradiation, air abrasion techniques, injection molding, embossing, and other techniques. The substrate materials are also generally selected for their compatibility with the full range of conditions to which the microfluidic devices may be exposed, including extremes of pH, temperature, salt concentration, and application of illumination or electric fields. Accordingly, in some preferred aspects, the substrate material may include silica based substrates, such as borosilicate glass, quartz, as well as other substrate materials.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction.

The channels and/or chambers of the microfluidic devices are typically fabricated into the upper surface of the first substrate, as microscale channels (e.g., grooves, indentations) using the above described microfabrication techniques. The first substrate comprises a top side having a first planar surface and a bottom side. In the microfluidic devices prepared in accordance with the methods described herein, the plurality of channels (e.g., grooves and/or indentations) are formed on the first planar surface. In some instances, the channels (e.g., grooves and/or indentations) formed in the first planar surface (prior to adding a second substrate) has bottom and side walls with the top remaining open. In some instances, the channels (e.g., grooves and/or indentations) in the first planar surface (prior to adding a second substrate) has bottom and side walls and the top remaining closed. In some instances, the channels (e.g., grooves and/or indentations) in the first planar surfaces (prior to adding a second substrate) has only side walls and no top or bottom surface.

When the first planar surface of the first substrate is placed into contact with, and bonded to the planar surface of the second substrate, the second substrate can cover and/or seal the grooves and/or indentations in the surface of the first substrate, to form the channels and/or chambers (e.g., the interior portion) of the device at the interface of these two components.

After the first substrate is bonded to a second substrate, the structure can further placed into contact with and bonded to a third substrate. The third substrate can be placed into contact with the side of the first substrate that is not in contact with the second substrate. In some embodiments, the first substrate is placed between the second substrate and the third substrate. In some embodiments, the second substrate and the third substrate can cover and/or seal the grooves, indentations, or apertures on the first substrate to form the channels and/or chambers (e.g., the interior portion) of the device at the interface of these components.

The device can have openings that are oriented such that they are in communication with at least one of the channels and/or chambers formed in the interior portion of the device from the grooves or indentations. In some embodiments, the openings are formed on the first substrate. In some embodiments, the openings are formed on the first and the second substrate. In some embodiments, the openings are formed on the first, the second, and the third substrate. In some embodiments, the openings are positioned at the top side of the device. In some embodiments, the openings are positioned at the bottom side of the device. In some embodiments, the openings are positioned at the first and/or the second ends of the device, and the channels run along the direction from the first end to the second end.

Conditions under which substrates may be bonded together are generally widely understood, and such bonding of substrates is generally carried out by any of a number of methods, which may vary depending upon the nature of the substrate materials used. For example, thermal bonding of substrates may be applied to a number of substrate materials, including, e.g., glass or silica based substrates, as well as polymer based substrates. Such thermal bonding typically comprises mating together the substrates that are to be bonded, under conditions of elevated temperature and, in some cases, application of external pressure. The precise temperatures and pressures will generally vary depending upon the nature of the substrate materials used.

For example, for silica-based substrate materials, i.e., glass (borosilicate glass, Pyrex™, soda lime glass, etc.), quartz, and the like, thermal bonding of substrates is typically carried out at temperatures ranging from about 500° C. to about 1400° C., and preferably, from about 500° C. to about 1200° C. For example, soda lime glass is typically bonded at temperatures around 550° C., whereas borosilicate glass typically is thermally bonded at or near 800° C. Quartz substrates, on the other hand, are typically thermally bonded at temperatures at or near 1200° C. These bonding temperatures are typically achieved by placing the substrates to be bonded into high temperature annealing ovens.

Polymeric substrates that are thermally bonded, on the other hand, will typically utilize lower temperatures and/or pressures than silica-based substrates, in order to prevent excessive melting of the substrates and/or distortion, e.g., flattening of the interior portion of the device, i.e., channels or chambers. Generally, such elevated temperatures for bonding polymeric substrates will vary from about 80° C. to about 200° C., depending upon the polymeric material used, and will preferably be between about 90° C. and 150° C. Because of the significantly reduced temperatures required for bonding polymeric substrates, such bonding may typically be carried out without the need for high temperature ovens, as used in the bonding of silica-based substrates. This allows incorporation of a heat source within a single integrated bonding system, as described in greater detail below.

Adhesives may also be used to bond substrates together according to well known methods, which typically comprise applying a layer of adhesive between the substrates that are to be bonded and pressing them together until the adhesive sets. A variety of adhesives may be used in accordance with these methods, including, e.g., UV curable adhesives, that are commercially available. Alternative methods may also be used to bond substrates together in accordance with the present invention, including e.g., acoustic or ultrasonic welding and/or solvent welding of polymeric parts.

Typically, a number of the described microfluidic chips or devices will be manufactured at a time. For example, polymeric substrates may be stamped or molded in large separable sheets which can be mated and bonded together. Individual devices or bonded substrates may then be separated from the larger sheet. Similarly, for silica-based substrates, individual devices can be fabricated from larger substrate wafers or plates, allowing higher throughput of the manufacturing process. Specifically, a number of channel structures can be manufactured into a first substrate wafer or plate which is then overlaid with a second substrate wafer or plate, and optionally further overlaid with a third substrate wafer or plate. The resulting multiple devices are then segmented from the larger substrates using known methods, such as sawing, scribing and breaking, and the like.

As noted above, the top or second substrate is overlaid upon the bottom or first substrate to seal the various channels and chambers. In carrying out the bonding process according to the methods of the present invention, the bonding of the first and second substrates is carried out using vacuum to maintain the two substrate surfaces in optimal contact. In particular, the bottom substrate may be maintained in optimal contact with the top substrate by mating the planar surface of the bottom substrate with the planar surface of the top substrate, and applying a vacuum through the holes that are disposed through the top substrate. Typically, application of a vacuum to the holes in the top substrate is carried out by placing the top substrate on a vacuum chuck, which typically comprises a mounting table or surface, having an integrated vacuum source. In the case of silica-based substrates, the bonded substrates are subjected to elevated temperatures in order to create an initial bond, so that the bonded substrates may then be transferred to the annealing oven, without any shifting relative to each other.

Alternate bonding systems for incorporation with the apparatus described herein include, e.g., adhesive dispensing systems, for applying adhesive layers between the two planar surfaces of the substrates. This may be done by applying the adhesive layer prior to mating the substrates, or by placing an amount of the adhesive at one edge of the adjoining substrates, and allowing the wicking action of the two mated substrates to draw the adhesive across the space between the two substrates.

In certain embodiments, the overall bonding system can include automatable systems for placing the top and bottom substrates on the mounting surface and aligning them for subsequent bonding Typically, such systems include translation systems for moving either the mounting surface or one or more of the top and bottom substrates relative to each other. For example, robotic systems may be used to lift, translate and place each of the top and bottom substrates upon the mounting table, and within the alignment structures, in turn. Following the bonding process, such systems also can remove the finished product from the mounting surface and transfer these mated substrates to a subsequent operation, e.g., separation operation, annealing oven for silica-based substrates, etc., prior to placing additional substrates thereon for bonding.

In some instances, the manufacturing of the microfluidic chip includes the layering or laminating of two or more layers of substrates, in order to produce the chip. For example, in microfluidic devices, the microfluidic elements of the device are typically produced by laser irradiation, etching or otherwise fabricating features into the surface of a first substrate. A second substrate is then laminated or bonded to the surface of the first to seal these features and provide the fluidic elements of the device, e.g., the fluid channels.

EXAMPLES

These examples are provided for illustrative purposes only and not to limit the scope of the claims provided herein.

Example 1

Figure 8:
FIG. 8 illustrates visualization of cluster amplification in a capillary lumen.

Nucleic acid clusters were established within a capillary and subjected to fluorescence imaging. A flow device having a capillary tube was used for the test. The resulting cluster images were presented in FIG. 8. The figure demonstrated that clusters within the lumen of a capillary system as disclosed herein can be reliably amplified and visualized.

Example 2

Figure 9A:
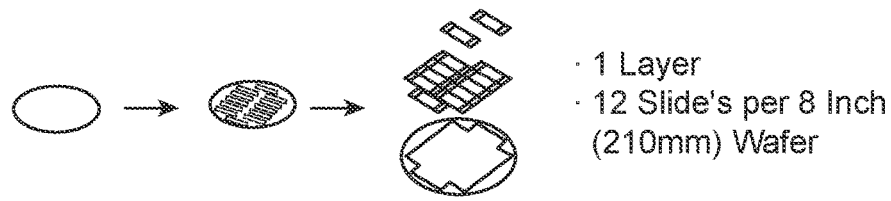
FIG. 9A-9C illustrates non-limiting examples of flow cell device preparation.
Figure 9B:
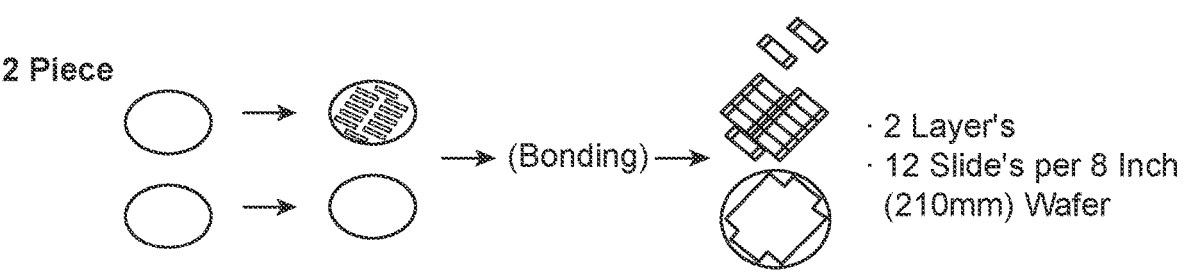
Figure 9C:
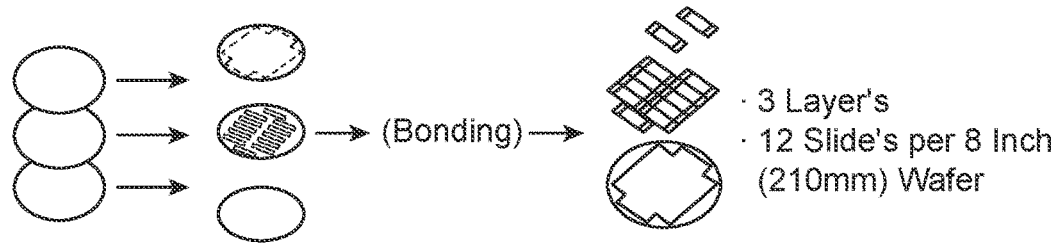

Flow cell device can be constructed from one, two, or three layer of glasses using one of the steps as shown in FIG. 9. In FIG. 9, the flow cell devices can be made form one, two, or three layers of glasses. The glasses can be either quarts or borosilicate glass. FIGS. 9A-9C show the methods to make such devices at wafer level with technologies such as focused femtosecond laser radiation (1 piece) and/or laser glass bonding (2 or 3 piece construction).

In FIG. 9A, the first layer of wafer is processed with a laser (e.g., femtosecond laser radiation) to ablate the wafer material and provide a patterned surface. The patterned surface can be a plurality of channels on the surface such as 12 channels per wafer. The wafer has a diameter of 210 mm. The processed wafer can be then placed on a support plate to form channels that can be used to direct fluid flow through a particular direction.

In FIG. 9B, the first layer of wafer having a patterned surface can be placed in contact with and bonded to a second layer of wafer. The bonding can be performed using a laser glass bonding technology. The second layer can cover and/or seal the grooves, indentations, or apertures on the wafer having the patterned surface to form the channels and/or chambers (e.g., the interior portion) of the device at the interface of these components. The bonded structure with two layers of wafer can then be placed on a support plate. The patterned surface can be a plurality of channels on the surface such as 12 channels per wafer. The wafer can have a diameter of 210 mm.

In FIG. 9C, the first layer of wafer having a patterned surface can be placed in contact with and bonded to a second layer of wafer on one side, and a third layer of wafer can be bonded to the first wafer layer on the other side so that the first player of wafer is positioned between the second and the third layers of wafer. The bonding can be performed using a laser glass bonding technology. The second layer and the third layer of wafers can cover and/or seal the grooves, indentations, or apertures on the wafer having the patterned surface to form the channels and/or chambers (e.g., the interior portion) of the device. The bonded structure with three layers of wafer can then be placed on a support plate. The patterned surface can be a plurality of channels on the surface such as 12 channels per wafer. The wafer can have a diameter of 210 mm.

Example 3

Figure 10A:
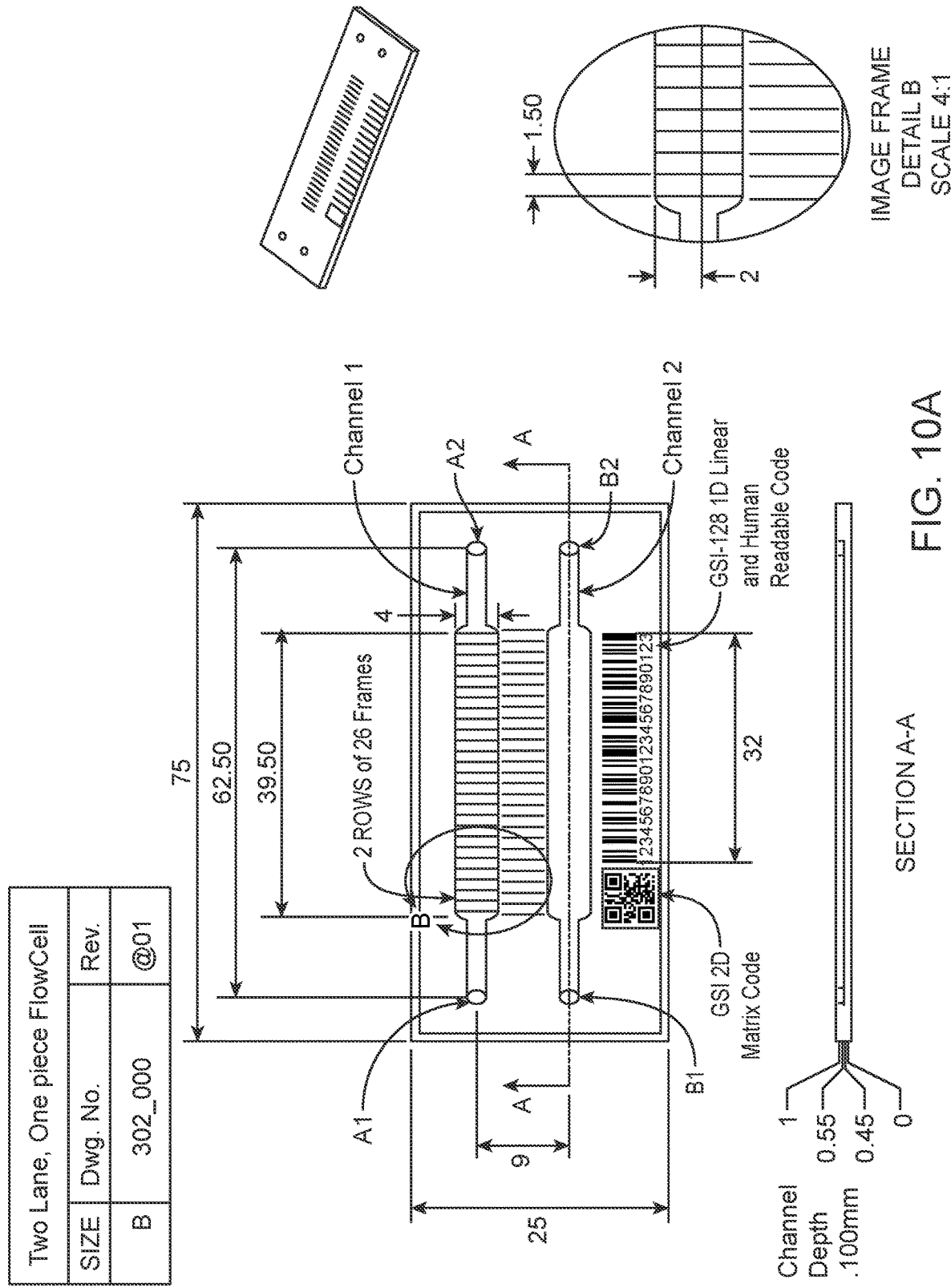
FIG. 10A-10C illustrates non-limiting examples of glass flow cell designs.

FIG. 10A shows a one-piece glass flow cell design. In this design, flow channels and inlet outlet holes can be fabricated using focused femtosecond laser radiation method. There are two channels/lanes on the flow cell, and each channel has 2 rows with 26 frames in each row. The channel can have a depth of about 100 µm. Chanel 1 has an inlet hole A1 and an outlet hole A2, and channel 2 has an inlet hole B1 and an outlet hole B2. The flow cell can also have a 1D linear and human readable code, and optionally a 2D matrix code.

Figure 10B:
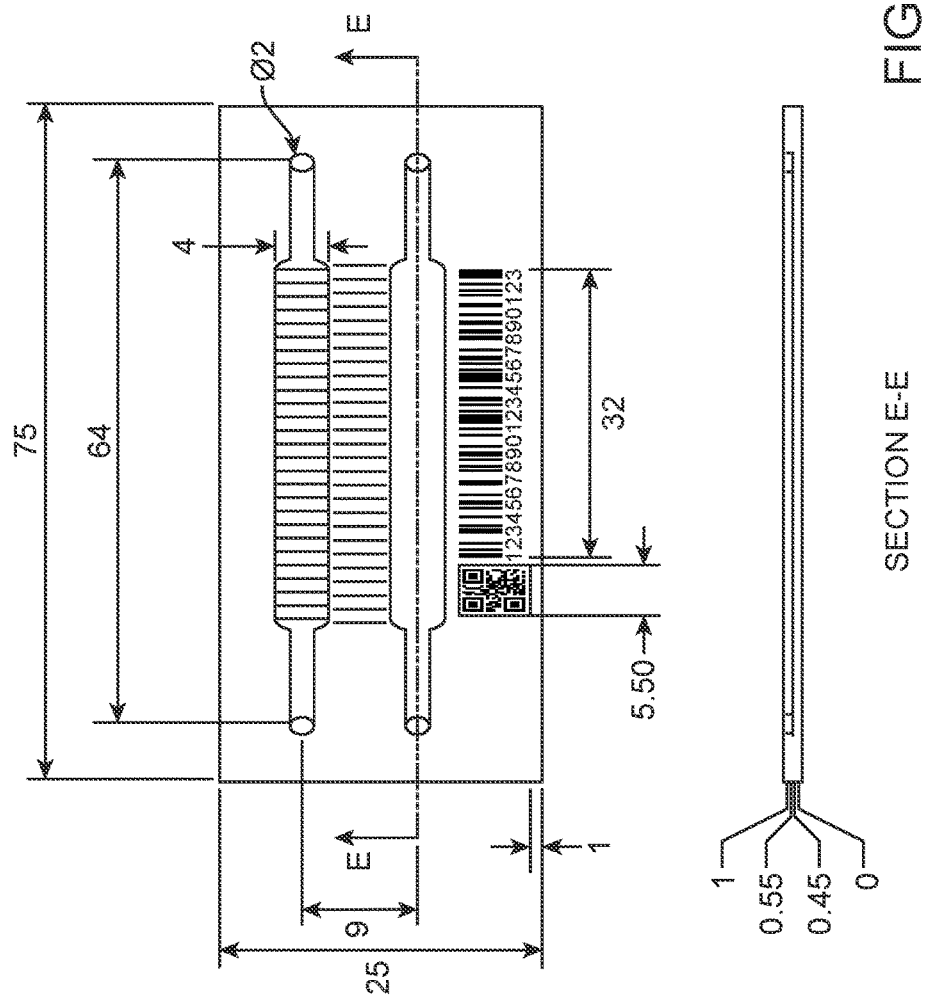

FIG. 10B shows a two-piece glass flow cell. In this design, flow channels and inlet and outlet holes can be fabricated using focused femtosecond laser radiation or chemical etching technology. The 2 pieces can be bonded together with laser glass bonding technology. The inlet and outlet holes can be positioned on the top layer of the structure and oriented in a way such that they are in communication with at least one of the channels and/or chambers formed in the interior portion of the device. There are two channels on the cell, and each channel has 2 rows with 26 frames in each row. The channel can have a depth of about 100 µm. Chanel 1 has an inlet hole A1 and an outlet hole A2, and channel 2 has an inlet hole B1 and an outlet hole B2. The flow cell can also have a 1D linear and human readable code, and optionally a 2D matrix code.

Figure 10C:
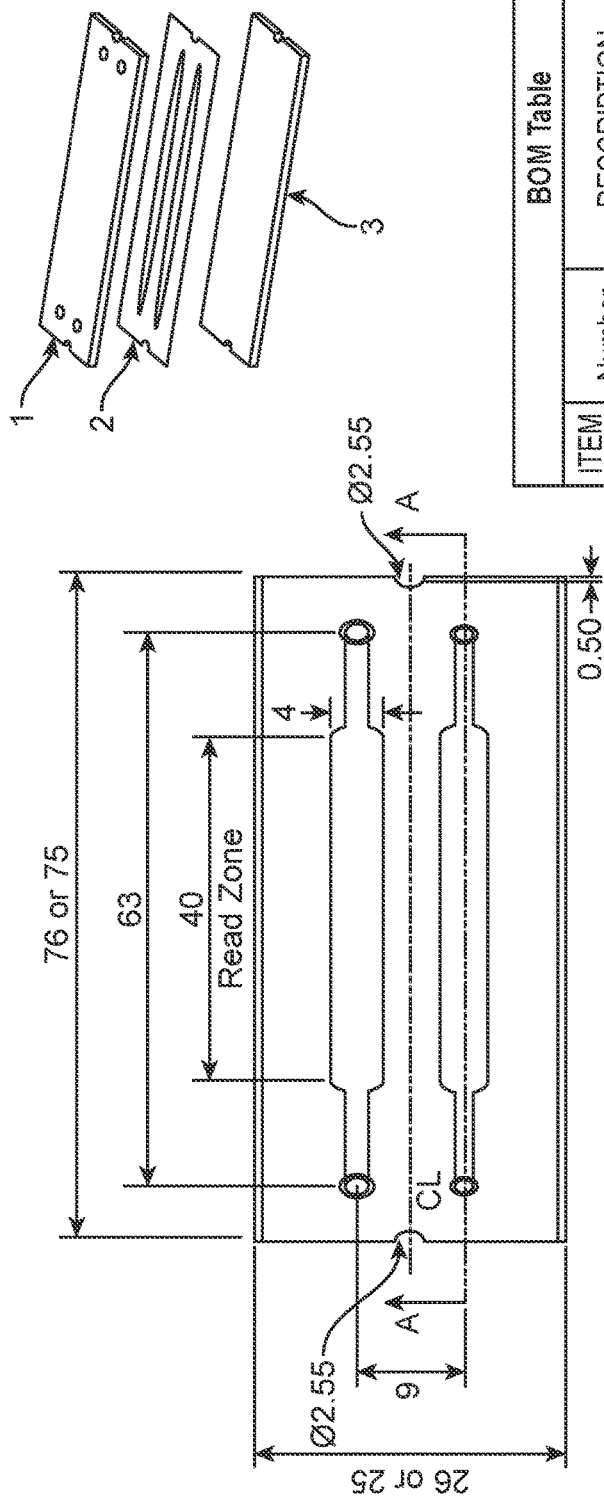
Figure 10C:
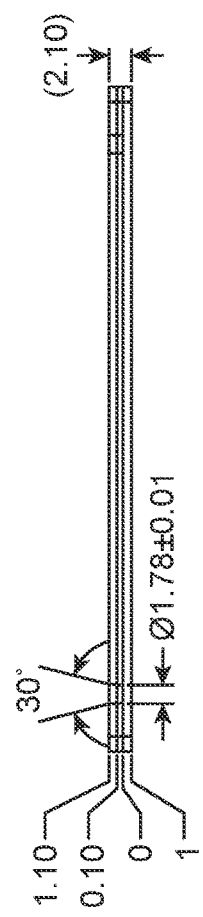

FIG. 10C shows a three-piece glass flow cell. In this design, flow channels and inlet and outlet holes can be fabricated using focused femtosecond laser radiation or chemical etching technology. The 3 pieces can be bonded together with laser glass bonding technology. The first layer of wafer having a patterned surface can be bonded to a second layer of wafer on one side, and a third layer of wafer can be bonded to the first wafer layer on the other side so that the first player of wafer is positioned between the second and the third layers of wafer. The inlet and outlet holes can be positioned on the top layer of the structure and oriented in a way such that they are in communication with at least one of the channels and/or chambers formed in the interior portion of the device. There are two channels on the cell, and each channel has 2 rows with 26 frames in each row. The channel can have a depth of about 100 µm. Chanel 1 has an inlet hole A1 and an outlet hole A2, and channel 2 has an inlet hole B1 and an outlet hole B2. The flow cell can also have a 1D linear and human readable code, and optionally a 2D matrix code.

Example 4

Flow cells were coated by washing prepared glass channels with KOH followed by rinsing with ethanol and silanization for 30 minutes at 65° C. Channel surfaces were activated with EDC-NHS for 30 min. followed by grafting of primers by incubation with 5 µm primer for 20 min., and then passivation with 30 µm PEG-NH2.

Multilayer surfaces are made following the approach of Example 4, where following PEG passivation, a multi-armed PEG-NHS is flowed through the channels following addition of the PEG-NH2, optionally followed by another incubation with PEG-NHS, and optionally another incubation with multi-armed PEG-NH2. For these surfaces, primer may be grafted at any step, especially following the last addition of multi-armed PEG-NH2.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A method of processing a sample of a subject having or suspected of having Coronavirus Disease 2019 (COVID-19) caused by a severe respiratory syndrome 2 (SARS-CoV-2) virus, said method comprising:
   (a) providing a nucleic acid sequencing flow cell comprising two or more microfluidic channels, wherein at least one of said two or more microfluidic channels comprises a surface comprising a nucleic acid sequence immobilized thereto, wherein said nucleic acid sequence is derived from said sample of said subject having or suspected of having said COVID-19;
   (b) contacting said nucleic acid sequence with a primer having complementarity with said nucleic acid sequence, to yield a primed nucleic acid sequence;
   (c) using at least (i) a polymerizing enzyme and (ii) a plurality of nucleobases having a plurality of detectable labels to subject said primed nucleic acid sequence to a primer extension reaction;
   (d) while performing said primer extension reaction, using a detector to detect a plurality of signals from at least a subset of said plurality of detectable labels; and
   (e) using said plurality of signals detected in (d) to generate sequencing data;
   (f) using one or more logic circuits to process said sequencing data in parallel to identify said nucleic acid sequence; and
   (g) using said nucleic acid sequence identified in (f) to determine that said sample contains a messenger ribonucleic acid (mRNA) molecule encoding said SARS-CoV-2.

2. The method of claim 1, wherein said plurality of detectable labels comprises a plurality of fluorophores.

3. The method of claim 1, wherein said using said plurality of signals detected in (d) to identify said nucleic acid sequence comprises imaging a first surface and an axially-displaced second surface of said two or more microfluidic channels using a fluorescent imaging system.

4. The method of claim 1, further comprising, before (a): (h) introducing a fluid composition comprising said nucleic acid sequence at a concentration of between about 0.5 nanomolar (nM) and 900 nM to said nucleic acid sequencing flow cell.

5. The method of claim 1, further comprising, before (a):
(i) hybridizing at least a portion of said nucleic acid sequence to at least a portion of oligonucleotides grafted to said surface.

6. The method of claim 4, wherein said nucleic acid sequencing flow cell is loaded with said fluid composition prior to (c).

7. The method of claim 1, wherein said nucleic acid sequence is present at said surface at a surface density comprising at least 4,000 molecules per square micrometer ($\mu m^2$).

8. The method of claim 5, wherein said surface is silanized and said oligonucleotides are covalently grafted to said surface.

9. The method of claim 1, wherein at least one of said two or more microfluidic channels is configured to hold a fluid volume between about 10 to about 300 microliters.

10. The method of claim 1, wherein a fluorescent image of said surface exhibits a contrast-to-noise ratio of at least or equal to about 5 when said fluorescent image of said surface is obtained with an inverted fluorescence microscope and a camera under non-signal saturating conditions while said surface is immersed in a buffer, and said plurality of detectable labels comprise Cyanine dye-3.

11. The method of claim 1, wherein said nucleic acid sequence has a length comprising more than or equal to about 100 base pairs.

12. The method of claim 1, wherein said nucleic acid sequencing flow cell comprises a flow cell cartridge that mates with a microfluidic chip.

13. The method of claim 1, further comprising, before (a):
(j) extracting said mRNA from said sample; and
(k) converting said mRNA to complementary DNA comprising said nucleic acid sequence.

14. The method of claim 1, wherein said sample comprises epithelial cells.

15. The method of claim 1, wherein said one or more logic circuits comprises a field programmable gate array (FPGA).

16. The method of claim 1, wherein said sequencing data is further analyzed using a central processing unit (CPU).

17. The method of claim 1, wherein using said one or more logic circuits to process said sequencing data in parallel is performed with Cloud-based computing.

18. The method of claim 1, wherein said two or more microfluidic channels comprises four microfluidic channels.

19. The method of claim 1, further comprising amplifying said nucleic acid sequence prior to (a) or (b) using polymerase chain reaction (PCR).

20. The method of claim 1, wherein said performing said primer extension reaction comprises performing a sequencing-by-synthesis reaction.

* * * * *